United States Patent
Lee et al.

(10) Patent No.: US 9,249,221 B2
(45) Date of Patent: Feb. 2, 2016

(54) HUMANIZED AND AFFINITY-MATURED ANTI-C-MET ANTIBODY AND USES THEREOF

(71) Applicant: Samsung Electronics Co., Ltd., Suwon-si, Gyeonggi-do (KR)

(72) Inventors: Seung Hyun Lee, Suwon-si (KR); Kyung Ah Kim, Seongnam-si (KR); Kwang Ho Cheong, Seoul (KR); Ho Yeong Song, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/231,470

(22) Filed: Mar. 31, 2014

(65) Prior Publication Data

US 2014/0294814 A1    Oct. 2, 2014

(30) Foreign Application Priority Data

Mar. 29, 2013  (KR) .......................... 10-2013-0034889

(51) Int. Cl.
*A61K 39/395* (2006.01)
*C07K 16/28* (2006.01)
*C07K 16/30* (2006.01)

(52) U.S. Cl.
CPC ......... *C07K 16/2863* (2013.01); *C07K 16/3023* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,563,696 B2* | 10/2013 | Cheong et al. | 530/388.22 |
| 8,900,582 B2* | 12/2014 | Cheong et al. | 424/133.1 |
| 2009/0280116 A1 | 11/2009 | Smith et al. | |
| 2011/0104176 A1 | 5/2011 | Cheong et al. | |
| 2012/0064085 A1 | 3/2012 | Bradbury | |
| 2012/0100152 A1 | 4/2012 | Roberts et al. | |
| 2012/0121512 A1 | 5/2012 | Grompe et al. | |
| 2013/0089542 A1* | 4/2013 | Lee et al. | 424/133.1 |
| 2015/0010575 A1* | 1/2015 | Kim et al. | 424/158.1 |
| 2015/0037328 A1* | 2/2015 | Liu et al. | 424/133.1 |

FOREIGN PATENT DOCUMENTS

KR   2011-0047698 A   5/2011

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Ezzell (J. NIH Res. 1995 7:46).*
Spitler (Cancer Biotherapy, 1995, 10:1-3).*
Boon (Adv. Can. Res. 1992 58:177-210).*

* cited by examiner

*Primary Examiner* — Sheela J Huff
(74) *Attorney, Agent, or Firm* — Leydig, Voit & Mayer, Ltd.

(57) ABSTRACT

Provided is a humanized and affinity-matured anti-c-Met antibody, a pharmaceutical composition including the antibody, and a method of preventing and/or treating c-Met-related disease using the antibody.

11 Claims, 14 Drawing Sheets

FIG. 1

DNA: GATATTGTGATGACTCAGTCTCCACTCTCCCTGCCCGTCACCCCTGGAGAG
+1:  D  I  V  M  T  Q  S  P  L  S  L  P  V  T  P  G  E

DNA: CCGGCCTCCATCTCCTGCAAGTCTAGTCAGAGTCTTTTATACAGTGGCAA
+1:  P  A  S  I  S  C  K  S  S  Q  S  L  L  Y  S  G  N

DNA: CAAAAGAACTACTTGGCTTGGTACCTGCAGAAGCCAGGGCAGTCTCCACAG
+1:  Q  K  N  Y  L  A  W  Y  L  Q  K  P  G  Q  S  P  Q

DNA: CTCCTGATCTATTGGGCATCTACTCGGGAATCTGGGGTCCCTGACAGGTTC
+1:  L  L  I  Y  W  A  S  T  R  E  S  G  V  P  D  R  F

DNA: AGTGGCAGTGGATCAGGCACAGATTTTACACTGAAAATCAGCAGAGTGGAG
+1:  S  G  S  G  S  G  T  D  F  T  L  K  I  S  R  V  E

DNA: GCTGAGGATGTTGGGGTTTATTACTGCCAGCAGTCTTATAGTGCTCCGCTC
+1:  A  E  D  V  G  V  Y  Y  C  Q  Q  S  Y  S  A  P  L

DNA: ACGTTTGGCCAGGGGACCAAGCTGGAGATCAAACGA
+1:  T  F  G  Q  G  T  K  L  E  I  K  R

DNA sequence: SEQ ID NO: 36
Amino aicd sequence: SEQ ID NO: 39

FIG. 2

```
DNA: GAGGTGCAGCTGGTGGAGTCTGGGGGAGGCTTGGTCCAGCCTGGAGGGTCC
 +1: E  V  Q  L  V  E  S  G  G  G  L  V  Q  P  G  G  S

DNA: CTGAGACTCTCCTGTGCAGCCTCTGGATTCACCTTTGATTACTACATGATA
 +1: L  R  L  S  C  A  A  S  G  F  T  F  D  Y  Y  M  I

DNA: AGCTGGGTCCGCCAGGCTCCAGGGAAGGGGCTGGAGTGGGTTGGCTTTATT
 +1: S  W  V  R  Q  A  P  G  K  G  L  E  W  V  G  F  I

DNA: AGAAACAAAGCTAACGGTTACACAACAGAGTACAGTGCATCTGTGAAGGGC
 +1: R  N  K  A  N  G  Y  T  T  E  Y  S  A  S  V  K  G

DNA: AGATTCACCATCTCAAGAGATGATTCAAAGAACTCACTGTATCTGCAAATG
 +1: R  F  T  I  S  R  D  D  S  K  N  S  L  Y  L  Q  M

DNA: AACAGCCTGAAAACCGAGGACACGGCCGTGTATTACTGTGCTAGACATAAC
 +1: N  S  L  K  T  E  D  T  A  V  Y  Y  C  A  R  D  N

DNA: TGGTTCGCTTACTGGGGCCAGGGCACCCTGGTCACCGTCTCCTCA
 +1: W  F  A  Y  W  G  Q  G  T  L  V  T  V  S  S
```

DNA sequence: SEQ ID NO. 38
Amino acid sequence: SEQ ID NO. 40

VH
```
chAbF46  EVKLVESGGGLVQPGGSLRLSCATSGFTFT DYYM HVRQPPGKALEWLG FIRNKANGYTT
L1bA     EVQLVESGGGLVQPGGSLRLSCAASGFTFT DYYI HVRQAPGKGLEWVG FIRNKANGYTT
C28      EVQLVESGGGLVQPGGSLRLSCAASGFTFT DYYI HVRQAPGKGLEWVG FIRNKANGYTT
C30      EVQLVESGGGLVQPGGSLRLSCAASGFTFT DYYI HVRQAPGKGLEWVG FIRNKANGYTT
1-F3     EVQLVESGGGLVQPGGSLRLSCAASGFTFT DYYI HVRQAPGKGLEWVG FIRNKANGYTT
C28m     EVQLVESGGGLVQPGGSLRLSCAASGFTFT DYYI HVRQAPGKGLEWVG FIRNKANGYTT chAbF46  EYSASVK RFTISRDNSQSILYLQMDTLAAEDSATYYCAR HWFAI WGQGTLVTVSA
L1bA     EYSASVK RFTISRDDSKNSLYLQMNSLKTEDTAVYYCAR HWFAI WGQGTLVTVSS
C28      EYSASVK RFTISRDDSKNSLYLQMNSLKTEDTAVYYCAR HWFAI WGQGTLVTVSS
C30      EYSASVK RFTISRDDSKNSLYLQMNSLKTEDTAVYYCAR HWFAI WGQGTLVTVSS
1-F3     EYSASVK RFTISRDDSKNSLYLQMNSLKTEDTAVYYCAR HWFAI WGQGTLVTVSS
C28m     EYSASVK RFTISRDDSKNSLYLQMNSLKTEDTAVYYCAR HWFAI WGQGTLVTVSS
```
( VH of chAbF46: SEQ ID NO: 19; VH of L1bA, C28, C30, 1-F3 and C28m: SEQ ID NO: 13 )

VL
```
chAbF46  DIIMTQSPSSLTVSAGEKVTMSC KSSQSLLASGNQKNYLA WHQQKPGRSPKMLII WASTR
L1bA     DIVMTQSPLSLPVTPGEPASISC KSSQSLLASGNQKNYLA WYLQKPGQSPQLLIY WASTR
C28      DIVMTQSPLSLPVTPGEPASISC KSSQSLLASGNQKNYLA WYLQKPGQSPQLLIY WASTR
C30      DIVMTQSPLSLPVTPGEPASISC KSSQSLLASGNQKNYLA WYLQKPGQSPQLLIY WASTR
1-F3     DIVMTQSPLSLPVTPGEPASISC KSSQSLLASGNQKNYLA WYLQKPGQSPQLLIY WASTR
C28m     DIVMTQSPLSLPVTPGEPASISC KSSQSLLASGNQKNYLA WYLQKPGQSPQMLII WASTR chAbF46  VSGVPDRFIGSGSGTDFTLTINSVQAEDLAVYYC QQSYSRPL TFGAGTKLELKRT
L1bA     VSGVPDRFSGSGSGTDFTLKISRVEAEDVGVYYC QQSYSRPL TFGQGTKLEIKRT
C28      VSGVPDRFSGSGSGTDFTLKISRVEAEDVGVYYC QQSYSRPL TFGQGTKLEIKRT
C30      VSGVPDRFSGSGSGTDFTLKISRVEAEDVGVYYC QQSYSRPL TFGQGTKLEIKRT
1-F3     VSGVPDRFSGSGSGTDFTLKISRVEAEDVGVYYC QQSYSRPL TFGQGTKLEIKRT
C28m     VSGVPDRFSGSGSGTDFTLKISRVEAEDVGVYYC QQSYSRPL TFGQGTKLEIKRT
```
( VL of chAbF46: SEQ ID NO: 20; VL of L1bA: SEQ ID NO: 14; VL of C28: SEQ ID NO: 15
VL of C30: SEQ ID NO: 16; VL of 1-F3: SEQ ID NO: 17; VL of C28m: SEQ ID NO: 18 )

MKN45: efficacy

HUMANIZED AND AFFINITY-MATURED ANTI-C-MET ANTIBODY AND USES THEREOF

CROSS-REFERENCE TO RELATED APPLICATIONS

This application claims the benefit of Korean Patent Application No. 10-2013-0034889 filed on Mar. 29, 2013, with the Korean Intellectual Property Office, the entire disclosure of which is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 23,233 Byte ASCII (Text) file named "715711SequenceListing-Revised.txt" created on Jun. 17, 2015.

BACKGROUND OF THE INVENTION

1. Field

A humanized and affinity-matured anti-c-Met antibody, a pharmaceutical composition comprising the antibody, and a method of preventing and/or treating a c-Met-related disease using the antibody, are provided.

2. Description of the Related Art c-Met is a receptor for hepatocyte growth factor (HGF), which is a cytokine that binds the extracellular region of the c-Met receptor tyrosine kinase to induce cell division, movement, morphogenesis, and angiogenesis of various normal cells and tumor cells. c-Met is a representative receptor tyrosine kinase existing on the surface of cells, is itself a proto-oncogene, and is sometimes involved in various mechanisms related to cancer, such as cancer development, metastasis, migration, invasion, and angiogenesis, independent from its ligand, HGF. Thus, c-Met has been recently emerging as a new target for anti-cancer therapy.

In particular, c-Met is known to be involved in induction of resistance to commonly used anti-cancer drugs, and, thus, is regarded as important with respect to personalized treatments. Representative anti-cancer therapeutic drugs targeting epidermal growth factor receptor EGFR (ERBB1), i.e., Eribitux or Tarceva, work by blocking the signaling related to cancer development. In addition, Herceptin, which is well known as a breast cancer therapeutic drug, targets ERBB2 (HER2) and works by blocking the transduction of signals necessary for cell proliferation. Among patients resistant to the drugs described above, the signal transduction pathway that induces cell proliferation is not blocked due to the over-expression of c-Met. Thus, c-Met has emerged as a target of interest for many pharmaceutical companies.

Still, there is a desire for additional anti-c-Met antibodies and related methods and compositions.

BRIEF SUMMARY OF THE INVENTION

One embodiment provides an anti-c-Met antibody or an antigen binding fragment thereof comprising (a) a heavy chain variable region comprising at least one heavy chain complementarity determining region (CDR) selected from the group consisting of (i) a CDR-H1 comprising the amino acid sequence of SEQ ID NO: 1, (ii) a CDR-H2 comprising the amino acid sequence of SEQ ID NO: 2, and (iii) a CDR-H3 comprising the amino acid sequence of SEQ ID NO: 3; and/or (b) a light chain variable region comprising at least one light chain complementarity determining region (CDR) selected from the group consisting of (i) a CDR-L1 comprising the amino acid sequence of SEQ ID NO: 4, SEQ ID NO: 7, SEQ ID NO: 8, or SEQ ID NO: 9, (ii) a CDR-L2 comprising the amino acid sequence of SEQ ID NO: 5, SEQ ID NO: 10 or SEQ ID NO: 11, and (iii) a CDR-L3 comprising the amino acid sequence of SEQ ID NO: 6 or SEQ ID NO: 12.

Another embodiment provides a pharmaceutical composition comprising at least one selected from the group consisting of the anti-c-Met antibody and the antigen biding fragment thereof as an active ingredient.

Another embodiment provides a method of treating a cancer comprising administering at least one selected from the group consisting of the anti-c-Met antibody and the antigen biding fragment thereof to a patient in need of treating cancer.

BRIEF DESCRIPTION OF THE DRAWINGS

FIG. 1 shows DNA and protein sequences of a humanized light chain variable region (SEQ ID NOs: 36 and 39, respectively), wherein the underlined sequences correspond to CDRs which are defined by chothia numbering scheme.

FIG. 2 shows DNA and protein sequences of a humanized heavy chain variable region (SEQ ID NOs: 38 and 40, respectively), wherein the underlined sequences correspond to CDRs which are defined by chothia numbering scheme.

FIG. 5 illustrates CDR sequences of clones obtained during screening processes.

FIG. 6 illustrates CDR sequences of clones obtained during screening processes.

FIG. 12 illustrates sequences of heavy chain variable region and light chain variable region of the antibody finally prepared through humanization and affinity maturation, wherein the sequences in boxes correspond to CDRs which are defined by kabat numbering scheme.

DETAILED DESCRIPTION OF THE INVENTION

Figure 3:
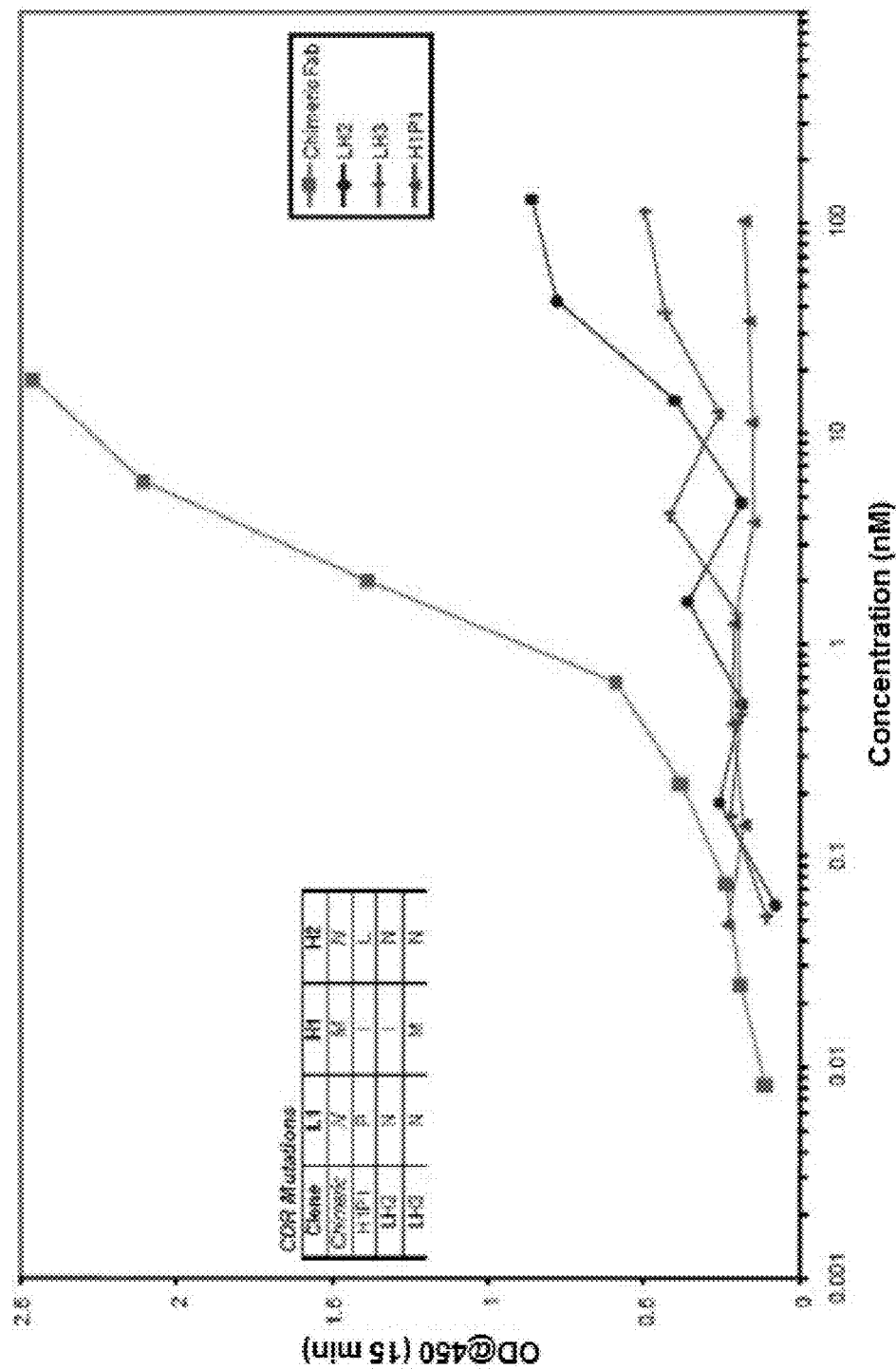
FIG. 3 is a graph showing binding degrees of Fabs derived from H1P1 to an antigen, c-Met ($NP_{13}000236$). Absorbance at OD 450 nm (15 min) is indicated on the y-axis, and concentration (nM) is indicated on the x-axis.

The term "c-Met" or "c-Met protein" refers to a receptor tyrosine kinase (RTK) which binds hepatocyte growth factor (HGF). c-Met may be a c-Met protein from any species, particularly a mammal, for instance, primates such as human c-Met (e.g., GenBank Accession Number NP_000236), or monkey c-Met (e.g., Macaca mulatta, GenBank Accession Number NP_001162100), or rodents such as mouse c-Met (e.g., GenBank Accession Number NP_032617.2), rat c-Met (e.g., GenBank Accession Number NP_113705.1), and the like. The c-Met protein may include a polypeptide encoded by the nucleotide sequence identified as GenBank Accession Number NM_000245, a polypeptide including the amino acid sequence identified as GenBank Accession Number NP_000236 or extracellular domains thereof. The receptor tyrosine kinase c-Met participates in various mechanisms, such as cancer development, metastasis, migration of cancer cell, invasion of cancer cell, angiogenesis, and the like.

The anti-c-Met antibody may also include a variant of the antibody. The variant of the antibody may be any isotype of antibodies derived from human (e.g., IgA, IgD, IgE, IgG1, IgG2, IgG3, IgG4, IgM, and the like) or other animals and/or one including any Fc region of antibodies derived from human (e.g., IgA, IgD, IgE, IgG1, IgG2, IgG3, IgG4, IgM, and the like) and other animals, having a mutated hinge, wherein at least one amino acid is changed, deleted or added. Unless stated otherwise, the anti-c-Met antibody may include the variants of the antibody, as well as the antibody with no variation.

Unless stated otherwise, the term "anti-c-Met antibody," as used herein, may be intended to mean an antibody or an antigen-binding fragment.

The anti-c-Met antibody may recognize a specific region of c-Met, e.g., a specific region of the SEMA domain, as an epitope. The anti-c-Met antibody may be any antibody or antigen-binding fragment that acts on c-Met to induce c-Met intracellular internalization and degradation.

c-Met, a receptor for hepatocyte growth factor (HGF), may be divided into three portions: extracellular, transmembrane, and intracellular. The extracellular portion is composed of an α-subunit and a β-subunit, which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 21, and is an extracellular domain that functions to bind HGF. A specific region of the SEMA domain, that is, a region including the amino acid sequence of SEQ ID NO: 22, which corresponds to a range from amino acid (a.a.) 106 to a.a. 124 of the amino acid sequence of SEQ ID NO: 21, is a loop region between the second and the third propellers within the epitopes of the SEMA domain. It acts as an epitope for the specific anti-c-Met antibody of the present invention.

The term "epitope," as used herein, refers to an antigenic determinant, which is a part of an antigen recognized by an antibody. In one embodiment, the epitope may be a region including 5 or more consecutive amino acid residues within the SEMA domain (SEQ ID NO: 21) of c-Met protein, for instance, 5 to 19 consecutive amino acid residues corresponding to a range from $106^{th}$ amino acid to $124^{th}$ amino acid within the SEMA domain (SEQ ID NO: 21) of a c-Met protein. For example, the epitope may be a polypeptide including 5 to 19 consecutive amino acids selected from among partial combinations of the amino acid sequence of SEQ ID NO: 22, with the amino sequence of SEQ ID NO: 24 (EEPSQ) serving as an essential element for the epitope. For example, the epitope may be a polypeptide including the amino acid sequence of SEQ ID NO: 22, SEQ ID NO: 23, or SEQ ID NO: 24.

The epitope including the amino acid sequence of SEQ ID NO: 23 corresponds to the outermost part of the loop between the second and third propellers within the SEMA domain of a c-Met protein. The epitope including the amino acid sequence of SEQ ID NO: 24 is a site to which the antibody or antigen-binding fragment according to one embodiment of the present invention most specifically binds.

Thus, the anti-c-Met antibody may specifically bind to an epitope which includes 5 to 19 consecutive amino acids, selected from among partial combinations of the amino acid sequence of SEQ ID NO: 22, including SEQ ID NO: 24 as an essential element. For example, the anti-c-Met antibody may be an antibody or an antigen-binding fragment that specifically binds to an epitope including the amino acid sequence of SEQ ID NO: 22, SEQ ID NO: 23, or SEQ ID NO: 24.

In one embodiment, the anti-c-Met antibody may be an antibody or antigen-binding fragment which comprises or consists essentially of:

(a) a heavy chain variable region comprising at least one heavy chain complementarity determining region (CDR) selected from the group consisting of (i) CDR-H1 comprising the amino acid sequence of SEQ ID NO: 1, (ii) CDR-H2 comprising the amino acid sequence of SEQ ID NO: 2, and (iii) CDR-H3 comprising the amino acid sequence of SEQ ID NO: 3; and/or (b) a light chain variable region comprising at least one light chain complementarity determining region (CDR) selected from the group consisting of (i) CDR-L1 comprising the amino acid sequence of SEQ ID NO: 4, SEQ ID NO: 7, SEQ ID NO: 8, or SEQ ID NO: 9, (ii) CDR-L2 comprising the amino acid sequence of SEQ ID NO: 5, SEQ ID NO: 10 or SEQ ID NO: 11, and (iii) CDR-L3 comprising the amino acid sequence of SEQ ID NO: 6 or SEQ ID NO: 12.

In particular, the anti-c-Met antibody may be an antibody or antigen-binding fragment which comprises:

(a) a heavy chain variable region comprising (i) CDR-H1 comprising the amino acid sequence of SEQ ID NO: 1, (ii) CDR-H2 comprising the amino acid sequence of SEQ ID NO: 2, and (iii) CDR-H3 comprising the amino acid sequence of SEQ ID NO: 3; and/or (b) a light chain variable region comprising (i) CDR-L1 comprising the amino acid sequence of SEQ ID NO: 4, SEQ ID NO: 7, SEQ ID NO: 8, or SEQ ID NO: 9, (ii) CDR-L2 comprising the amino acid sequence of SEQ ID NO: 5, SEQ ID NO: 10 or SEQ ID NO: 11, and (iii) CDR-L3 comprising the amino acid sequence of SEQ ID NO: 6 or SEQ ID NO: 12.

The amino acid sequences of the above CDRs may be defined by the kabat numbering scheme.

In an embodiment, the CDR-H1 may further comprise an amino acid sequence, for example, "GFTFT"(SEQ ID NO: 34), at the N-terminal end thereof, when the CDR-H1 is defined by other numbering scheme (e.g., chothia numbering scheme, etc) than kabat numbering scheme.

For example, the anti-c-Met antibody may be an antibody or antigen-binding fragment which comprises or consists essentially of:

(a) a heavy chain variable region comprising the amino acid sequence of SEQ ID NO: 13, and/or (b) a light chain variable region comprising the amino acid sequence of SEQ ID NO: 14, SEQ ID NO: 15, SEQ ID NO: 16, SEQ ID NO: 17, or SEQ ID NO: 18.

The anti-c-Met antibody may be one obtained by humanization and affinity maturation of mouse antibody AbF46 described in Korean Patent Publication No. 2011-0047698. The affinity of the antibody to the antigen is improved by modifying residues in the mouse antibody AbF46, such as residues of S27E position (positioned in L1) and A94 position (positioned in L3) of the light chain variable region (SEQ ID NO: 20) and M34 position (positioned in H1) of the heavy chain variable region (SEQ ID NO: 19), to any one selected from tryptophan (W; e.g., S27E->W), arginine (R; e.g., A94->R), and isoleucine (I; e.g., M34->I). In addition thereto, modification (e.g., substitution) of at least one position selected from the group consisting of G27F, N28, L33, S52, and S56 of the light chain variable region and T30, S62, and K64 of the heavy chain variable region with a different amino acid from the original, leads to more improved affinity of the antibody to the antigen.

Herein, the position of the amino acid within the CDRs is defined according to Kabat numbering.

The binding affinity (Kd) of the anti-c-Met antibody or an antigen-binding fragment thereof to the antigen, c-Met protein, may be 1 nM or less, for example, 0.00001 nM to 1 nM, or 0.2 nM or less, for example, 0.00001 nM to 0.2 nM.

Another embodiment provides an antibody or an antigen-binding fragment thereof, which binds to c-Met protein competitively with the anti-c-Met antibody or an antigen-binding fragment thereof. Such competitively binding antibody may recognize a region as an epitope, where the region is adjacent to the epitope positioned at SEMA domain in the three-dimensional configuration of c-Met protein. The binding affinity (Kd) of the competitively binding antibody may be 1 nM or less, for example, 0.00001 nM to 1 nM, or 0.2 nM or less, for example, 0.00001 nM to 0.2 nM.

Animal-derived antibodies produced by immunizing subject animals with a desired antigen generally invoke immunogenicity when injected into humans for the purpose of medical treatment, and, thus, chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies are developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDR of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and, thus, application of additional antibody engineering technology for recovering the antigen binding affinity is necessary.

The anti-c-Met antibodies may be mouse-derived antibodies, mouse-human chimeric antibodies, humanized antibodies, or human antibodies. The antibodies or antigen-binding fragments thereof may be isolated from (e.g., not be originally present in) a living body, or non-naturally occurring. The antibodies or antigen-binding fragments thereof may be recombinant or monoclonal.

An intact antibody includes two full-length light chains and two full-length heavy chains, in which each light chain is linked to a heavy chain by disulfide bonds. The antibody comprises a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain or fragments thereof, including a variable region VH that includes amino acid sequences sufficient to provide specificity to antigens, and three constant regions, CH1, CH2, and CH3, and a hinge. The term "light chain" refers to a full-length light chain or fragments thereof, including a variable region VL that includes amino acid sequences sufficient to provide specificity to antigens, and a constant region CL.

The term "complementarity determining region (CDR)" refers to an amino acid sequence found in a hyper variable region of a heavy chain or a light chain of immunoglobulin. The heavy and light chains may respectively include three CDRs (CDR-H1, CDR-H2, and CDR-H3; and CDR-L1, CDR-L2, and CDR-L3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

In one embodiment, the antibody may be an antigen-binding fragment selected from the group consisting of scFv, (scFv)$_2$, Fab, Fab', and F(ab')$_2$.

The term "antigen-binding fragment" used herein refers to fragments of an intact immunoglobulin including portions of a polypeptide including antigen-binding regions having the ability to specifically bind to the antigen. For example, the antigen-binding fragment may be scFv, (scFv)$_2$, Fab, Fab', or F(ab')$_2$, but is not limited thereto. Among the antigen-binding fragments, Fab that includes light chain and heavy chain variable regions, a light chain constant region, and a first heavy chain constant region CH1, includes one antigen-binding site. The Fab' fragment is different from the Fab fragment, in that Fab' includes a hinge region with at least one cysteine residue at the C-terminal of CH1. The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, addition, or substitution of at least one amino acid residue of the amino acid sequence of the hinge region so that it exhibits enhanced antigen-binding efficiency. For example, the antibody may comprise a hinge region comprising the amino acid sequence of SEQ ID NO: 25, SEQ ID NO: 26, SEQ ID NO: 27, SEQ ID NO: 28, or SEQ ID NO: 29, or a hinge region comprising the amino acid sequence of SEQ ID NO: 30 (non-modified human hinge). For example, the hinge region can comprise the amino acid sequence of SEQ ID NO: 25 or SEQ ID NO: 26.

An embodiment provides a pharmaceutical composition comprising the anti-c-Met antibody or antigen-binding fragment thereof as an active ingredient.

Another embodiment provides a pharmaceutical composition for preventing and/or treating a c-Met-related disease, comprising the anti-c-Met antibody or antigen-binding fragment thereof as an active ingredient. In particular, the pharmaceutical composition for preventing and/or treating a c-Met-related disease may comprise a pharmaceutically effective amount of the anti-c-Met antibody or antigen-binding fragment thereof, optionally together with a pharmaceutically acceptable vehicle, a diluent, and/or an excipient.

Another embodiment provides a method of inhibition of c-Met, comprising administering a pharmaceutically effective amount of the anti-c-Met antibody or antigen-binding fragment thereof, to a patient in need of inhibition of a c-Met. The inhibition of c-Met may include internalization and/or degradation of c-Met.

Another embodiment provides a method of preventing and/or treating a c-Met-related disease, comprising administering a pharmaceutically effective amount of the anti-c-Met antibody or antigen-binding fragment thereof, to a patient in need of preventing and/or treating a c-Met-related disease. The method may further comprise a step of identifying the patient in need of preventing and/or treating a c-Met-related disease, prior to the step of administering.

The patient may be an animal, or a cell or tissues obtained therefrom, wherein the animal may be selected from mammals, including human, dogs, cats, mice, and the like. In particular, the patient may be a mammal except human.

The c-Met-related disease may refer to any disease caused by the expression, overexpression, or abnormal activation of c-Met. Cancer is representative of a c-Met-related disease. Examples of the cancer include squamous cell carcinoma, small cell lung cancer, non-small cell lung cancer, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, chronic or acute leukemia, lymphocyte lymphoma, hepatoma, stomach cancer, pancreatic cancer, glioblastoma, cervical cancer, ovarian cancer, liver cancer, bladder cancer, hepatic tumor, breast cancer, colon cancer, large intestine cancer, endometrial cancer, uterine cancer, salivary gland cancer, renal cancer, prostate cancer, vulvar cancer, thyroid cancer, and head and neck cancer, but are not limited thereto. The cancer may include metastatic cancers as well as primary cancers. Gestational diabetes also falls within the scope of c-Met-related diseases. Thus, in addition to cancers, the c-Met-related disease may include gestational diabetes.

The term "pharmaceutically effective amount" or "therapeutically effective amount" may refer to a dosage necessary for obtaining a desired effect, for instance, inhibiting (degrading) c-Met, or preventing or treating c-Met-related diseases in a subject in need thereof, and may vary depending on various factors including a desired result, kinds of diseases or symptoms, the severity of illness, the route of administration, dosage forms, etc.

So long as it is usually used in drug formulations, any pharmaceutically acceptable vehicle may be contained in the pharmaceutical composition. Examples of the pharmaceutically acceptable vehicle available for the pharmaceutical composition may include one or more selected from the group consisting of lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but are not limited thereto. The pharmaceutical composition may further include an additive selected from the group consisting of a diluent, an excipient, a lubricant, a wetting agent, a sweetener, a flavorant, an emulsifier, a suspending agent, a preservative, and a combination thereof.

The anti-c-Met antibody or the pharmaceutical composition comprising a pharmaceutically effective amount of the anti-c-Met antibody may be administered orally or parenterally. For parenteral administration, the administration may be carried out via intravenous, subcutaneous, intramuscular, intraperitoneal, intradermal, local, intranasal, intrapulmonary, or intrarectal route, but is not limited thereto. For oral administration, the pharmaceutical composition may be preferably coated or formulated to protect the active ingredient from being degraded in the stomach because the peptides are digested by pepsin. In addition, the administration may be performed with the aid of an instrument adapted for delivering the pharmaceutical composition to target cells.

The administration dosage including the pharmaceutically effective amount of the anti-c-Met antibody may vary depending on various factors including the type of formulation, the patient's age, weight, and sex, the severity of the disorder being treated, diet, the time of administration, the route of administration, the rate of excretion, and sensitivity. For example, the pharmaceutical composition of the present invention may be administered at a single dose raging from about 0.001 mg to about 100 mg for adults, for example, from about 0.001 mg to about 0.1 mg, from about 0.1 mg to about 1 mg, from about 1 mg to about 10 mg, or from about 10 mg to about 100 mg.

According to a method that is well known to those skilled in the art, the anti-c-Met antibody or the pharmaceutical composition may be formulated, together with pharmaceutically acceptable carriers and/or excipients, into unit dose forms, or may be included within a multiple dose package. In this context, the pharmaceutical composition may be formulated into solutions in oil or aqueous media, suspensions, syrup, emulsions, elixirs, powders, granules, tablets, or capsules, and may further include a dispersant and/or a stabilizer.

The anti-c-Met antibody or the pharmaceutical composition may be administered alone or in combination with other therapeutics. In this case, they are administered sequentially or simultaneously together with conventional therapeutics.

The composition including an antibody or an antigen-binding fragment can be formulated into immunoliposomes. Liposomes including an antibody may be prepared using methods that are well-known in the art. The immunoliposomes may be produced from a lipid composition including phosphatidylcholine, cholesterol, and PEGylated phosphatidylethanolamine by reverse-phase evaporation. In one example, Fab' may be conjugated to liposomes by disulfide reformation. The liposome may further contain an anticancer agent such as doxorubicin.

In one embodiment, the antibody may act as an antagonist of c-Met protein.

As used herein, the term "antagonist" is intended to encompass all molecules that at least partially block, suppress, or neutralize at least one of the biological activities of a target (e.g., c-Met). By way of example, an "antagonist" antibody means an antibody that represents suppression or inhibition against the biological activity of the antigen to which the antibody binds (e.g., c-Met). An antagonist may function to reduce ligand-induced receptor phosphorylation or to incapacitate or kill cells which have been activated by ligands. Also, an antagonist may completely interfere with receptor-ligand interaction or substantially reduce the interaction by changing the three-dimensional structure of the receptor or by down regulation.

An additional embodiment provides a nucleic acid molecule encoding the anti-c-Met antibody or an antigen-binding fragment thereof comprising the heavy chain variable region or light chain variable region. Anotheraspect provides a recombinant vector comprising the nucleic acid molecule. A further aspect provides a recombinant cell transformed with the recombinant vector.

The term "vector" refers to a means for expressing a target gene in a host cell, as exemplified by a plasmid vector, a cozmid vector, and a viral vector such as a bacteriophage vector, adenovirus vector, retrovirus vector, and an adeno-related virus vector. The recombinant vector may be constructed from, but not limited to, well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔ.z1, M13, etc.) or viruses (for example, SV40, etc.) by manipulation.

In the recombinant vector, the nucleic acid molecule may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be constructed typically as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a pLλ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as a f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed in the present invention. Examples of the prokaryotic host cell available for the present invention include E. coli JM109, E. coli BL21, E. coli RR1, E. coli LE392, E. coli B, E. coli X 1776, E. coli W3110, Bacillus spp. such as Bacillus subtilis and Bacillus thuringiensis, and enterobacteriaceae strains such as Salmonella typhimurium, Serratia marcescens and various Pseudomonas species. Eukaryotic host cells to be transformed may be Saccharomyces cerevisiae, insect cells, and animal cells including, but not limited to Sp2/0, CHO (Chinese hamster ovary) K1, CHO DG44, PER.C6, W138, BHK, COS-7, 293, HepG2, Huh7, 3T3, RIN, and MDCK.

Using a method well known in the art, the polynucleotide or a recombinant vector comprising the polynucleotide may be introduced (incorporated) into a host cell. This transformation is carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

The anti-c-Met antibody and the composition or method for preventing and/or treating a c-Met-related disease provided by the present invention can lead to effective prevention and/or treatment of the disease.

One or more embodiments of the present invention will now be described in further detail with reference to the following Examples. However, these examples are for the illustrative purposes only and are not intended to limit the scope of the invention.

EXAMPLES

Example 1

Production of "AbF46," a Mouse Antibody to c-Met

(1) Immunization of Mice

To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and the equal volume of complete Freund's adjuvant. Two weeks after the injection, a second intraperitoneal injection was administered to the same mice with a mixture of 50 μg of human c-Met/Fc protein and the equal volume of incomplete Freund's adjuvant. One week after the second immunization, the immune response was finally boosted. Three days later, blood was taken from the tail, and the sera obtained from the blood were 1/1000 diluted in phosphate buffered saline (PBS) and used to examine a titer of antibody to c-Met by ELISA, indicating that the titer of antibody recognizing c-Met increases. Mice found to have a sufficient antibody titer were selected for use in the cell fusion process.

(2) Cell Fusion and Production of a Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen) to produce a cell suspension. The obtained cell suspension was centrifuged to recover the cell layer. The obtained splenocytes ($1 \times 10^8$ cells) were mixed with myeloma cells (Sp2/0) ($1 \times 10^8$ cells), and then centrifuged to yield a cell pellet. The cell pellet was slowly suspended, treated with 45% polyethylene glycol (PEG) (1 mL) in culture medium (DMEM) for 1 min at 37° C., and supplemented with 1 mL of DMEM. To the cells was added 10 mL of DMEM over 1 min, after which incubation was conducted in water at 37° C. for 5 min. Then the cell volume was adjusted to 50 mL before centrifugation. The cell pellet thus formed was resuspended at a density of $1~2 \times 10^5$ cells/mL in a selection medium (HAT medium) and 0.1 mL of the cell suspension was allocated to each well of 96-well plates, which were then incubated at 37° C. in a $CO_2$ incubator to establish a hybridoma cell population.

(3) Selection of Hybridoma Cells Producing Monoclonal Antibodies to c-Met Protein From the hybridoma cell population established in Example 1(2), hybridoma cells which showed a specific response only to c-Met protein were screened by ELISA using human c-Met/Fc fusion protein and human Fc protein as antigens.

Human c-Met/Fc fusion protein (R&D Systems) was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human IgG1 Fc protein was attached to the plate surface in the same manner.

The hybridoma cell culture obtained in Example 1(2) was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST. A substrate (OPD) of the peroxidase was added thereto, allowing the substrate and the peroxidase to react. The reaction level was determined by measuring absorbance at 450 nm on an ELISA reader. Hybridoma cell lines which secrete antibodies that specifically and strongly bind to human c-Met protein but not human Fc were selected repeatedly.

From the hybridoma cell lines obtained by the repeated selections, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, under Accession No. KCLRF-BP-00220 according to the Budapest Treaty (refer to Korean Patent Laid-Open Publication No. 2011-0047698, the disclosure of which is herein incorporated by reference in its entirety).

(4) Production and Purification of a Monoclonal Antibody

The hybridoma cell line obtained in Example 1(3) was cultured in a serum-free medium, and the monoclonal antibody was produced and purified from the cell culture.

First, the hybridoma cells were cultured in 50 mL of a medium (DMEM) supplemented with 10% (v/v) fetal bovine serum (FBS) and centrifuged to precipitate the cells. The obtained cell pellet was washed twice or more with 20 mL of PBS and, then, the FBS was removed therefrom. Then, the cells were resuspended in 50 mL of DMEM and incubated for 3 days at 37° C. in a $CO_2$ incubator. After removing the cells producing the antibody by centrifugation, the supernatant containing the secreted antibody was collected, and either stored at 4° C. or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody was stored in PBS before use in the following examples. The separated and purified antibody was named as mouse antibody AbF46.

Example 2

Cloning of the AbF46 Variable Region

The amino acid sequence of mouse antibody AbF46 prepared in Example 1 was analyzed. The analyzed sequences of the light chain variable region (VL), heavy chain variable region (VH), and each CDR of antibody AbF46 are summarized in following Table 1:

TABLE 1

|  | Heavy chain | Light chain |
|---|---|---|
| Variable region | EVKLVESGGG LVQPGGSLRL<br>SCATSGFTFT DYYMSWVRQP<br>PGKALEWLGF IRNKANGYTT<br>EYSASVKGRF TISRDNSQSI<br>LYLQMDTLRA EDSATYYCAR<br>DNWFAYWGQG TLVTVSA<br>(SEQ ID NO: 19) | DILMTQSPSS LTVSAGEKVT<br>MSCKSSQSLL ASGNQNNYLA<br>WHQQKPGRSP KMLIIWASTR<br>VSGVPDRFIG SGSGTDFTLT<br>INSVQAEDLA VYYCQQSYSA<br>PLTFGAGTKL ELKRT<br>(SEQ ID NO: 20) |

TABLE 1-continued

|      | Heavy chain                    | Light chain                           |
|------|--------------------------------|---------------------------------------|
| CDR1 | DYYMS<br>(SEQ ID NO: 31)       | KSSQSLLASGNQNNYLA<br>(SEQ ID NO: 32)  |
| CDR2 | FIRNKANGYTTEYSASVKG<br>(SEQ ID NO: 2) | WASTRVS<br>(SEQ ID NO: 5)      |
| CDR3 | DNWFAY<br>(SEQ ID NO: 3)       | QQSYSAPLT<br>(SEQ ID NO: 33)          |

Based on the amino acid sequences, a single stranded DNA fragment encoding each of the heavy chain variable region and light chain variable region was prepared, and cloned into a phage-based vector (MabPrex) including the single stranded DNA fragment encoding constant region of human kappa light chain and CH1 of human IgG1, to prepare chimeric clones Example 3

Humanization of Antibody IgG AbF46

(1) Humanization of the Light Chain Variable Region

An alignment of the light chain variable region (VL; SEQ ID NO: 20) of the mouse antibody AbF46 with human antibody framework (using human germ line gene) was performed by Blast P search (BLASTp online database tool, maintained by the National Center for biotechnology Information (NCBI), Bethesda, MD). The results identified IGKV2-28*01 (amino acid sequence SEQ ID NO: 35; nucleic acid sequence; ACCESSION number: HC873376) as having high amino acid sequence identity/homology with the mouse antibody AbF46. Therefore, IGKV2-28*01 was selected and used as the human germ line. The CDR-L1 of IGKV2-28*01 is 16 aa in length, which is similar to the length (17 aa) of CDR-L1 of the mouse antibody AbF46. Thus, it was determined that IGKV2-28*01 is more appropriate for use in preparing a humanized antibody than other germ lines.

CDR-L1, CDR-L2, and CDR-L3 of the mouse antibody AbF46 were defined and numbered according to Kabat numbering. The DNA sequences of CDR-L1, CDR-L2, and CDR-L3 were derived from the mouse antibody AbF46. During synthesizing the DNA, N30 position of CDR-L1, which corresponds to $36^{th}$ position of the amino acid sequence (SEQ ID NO: 20) of the light chain variable region as shown in Table 1 in Example 2, was substituted with proline (P), and randomized in the following cloning process. The DNA and amino acid sequences of the humanized light chain variable region are shown in FIG. 1.

(2) Humanization of the Heavy Chain Variable Region

An alignment of the heavy chain variable region (VH; SEQ ID NO: 19) of the mouse antibody AbF46 with human antibody framework (using human germ line gene) was performed by Blast P search. The results identified IGHV3-72*01 (SEQ ID NO: 37) as having high amino acid sequence identity/homology with the mouse antibody AbF46. Therefore, IGHV3-72*01 was selected and used as the human germ line.

CDR-H2 and CDR-H3 were defined and numbered according to Kabat numbering and CDR-H1 was defined according to Chothia and numbered according to Kabat numbering. The DNA sequences of CDR-L1, CDR-L2, and CDR-L3 were derived from the mouse antibody AbF46.

During synthesizing the DNA, some positions of the CDRs were substituted as follows, and randomized in the following cloning process: the M34 position of CDR-H1 corresponding to $34^{th}$ position of the amino acid sequence (SEQ ID NO: 19) of the heavy chain variable region as shown in Table 1 was substituted with isoleucine (I); and the N53 position of CDR-H2 corresponding to $56^{th}$ position of amino acid sequence (SEQ ID NO: 19) of the heavy chain variable region as shown in Table 1 was substituted with leucine (L). The modification (substitution) at the M34 position was to remove the possibility of oxidation at the same position ($34^{th}$ position), and the modification at the N53 position was to avoid deamidation. The DNA and amino acid sequences of the humanized heavy chain variable region are shown in FIG. 2.

Example 4

Cloning of the Variable Region of Antibody AbF46 and Affinity Maturation

Single stranded DNA fragments encoding the variable regions of the humanized antibody AbF46 prepared in Example 3 were designed and synthesized. The designed and synthesized single stranded DNA fragments were cloned into a phage-based vector (MabPrex) including the single stranded DNA fragment encoding the constant region of human kappa light chain and CH1 of human IgG1.

According to the above process, a clone 'H1P1' (Fab fragment), which is completely humanized and includes all three modifications (substitutions) in CDRs as described in Example 3, was constructed. The CDR modifications in clone H1P1 are summarized as follows: N30P in CDR-L1, M34I in CDR-H1, and N53L in CDR-H2. That is, H1P1 is a clone having the genes of human germ lines of IGHV3-72*01 and IGKV2-28*01 as framework, and the modifications of N30P in CDR-L1, M34I in CDR-H1, and N53L in CDR-H2.

Clone H1P1 was cultured, and a small amount of Fab was released into periplasmic space of *E. coli* by osmotic shock. From ELISA results, it was found that clone H1P1 expresses Fab well, but is poor in binding to antigen, c-Met (NP_000236).

The above result indicates that the completely humanized antibody clone is good at expression but does not recognize the antigen well. Therefore, in order to recover the activity of binding to the antigen that was lost in the humanization process, back mutations where at least one of the CDR mutations was reversed to wild type were performed. For the back mutation, clone LH2 having only one mutation, M34I, in CDR-H1 of the mouse antibody AbF46, and clone LH3 having only one mutation, N30P, in CDR-L1 of the mouse antibody AbF46, were additionally constructed.

The clones obtained from such back mutations were subjected to antigen-binding assay (ELISA), and the obtained data are shown in FIG. 3.

The above result shows that the presence of asparagine (Asn) at the mutation site in CDR-L1 and CDR-H2 is important in binding to the antigen. Methionine (Met) in CDR-H1 also appears to be involved in binding to the antigen. However, considering that the antigen binding of LH2 is stronger than that of LH3, it appears that isoleucine (Ile) is a more suitable amino acid residue at the mutation site in CDR-H1. Clones LH2 and LH3 exhibited weak but reproducible binding abilities to the antigen, c-Met (NP_000236).

In order to establish CDR libraries (L2, L3, and H3) which are selected so that the binding intensity of the humanized clones to the antigen, c-Met ($NP_{13}000236$), can be enhanced, several libraries, wherein each of CDR-L2, CDR-L3, and CDR-H3 is randomized from a template, clone H1P1 or LH2 (having M34I mutation in CDR-H1 only), were constructed.

From the CDR libraries, the L3 library that is constructed based on clone LH2shows a positive spot on the filter lift (among 1,000 clones, about 10 clones show a positive spot). The clones were separated, and the sequences were analyzed. A binding assay was performed by ELISA, and the obtained result is shown in FIG. 4.

Figure 4:
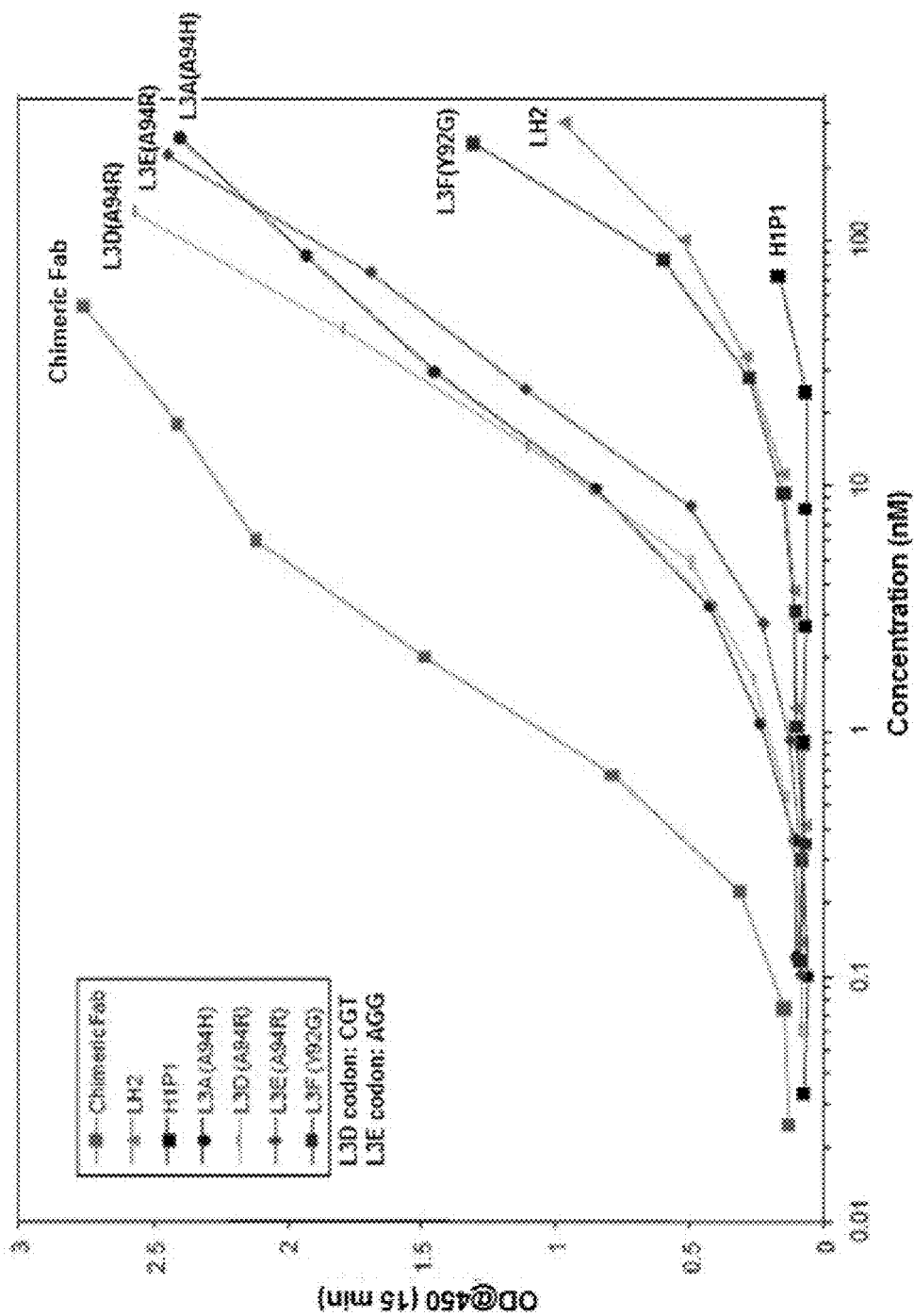
FIG. 4 is a graph showing binding degrees of humanized Fabs to the antigen, c-Met ($NP_{13}000236$). Absorbance at OD 450 nm (15 min) is indicated on the y-axis, and concentration (nM) is indicated on the x-axis.

As shown in FIG. 4, the single mutation at the 94$^{th}$ position in CDR-L3 corresponding to 100$^{th}$ position of the light chain variable amino acid sequence (SEQ ID NO: 20) in Table 1 leads to a considerable increase in the binding ability of the humanized clone to the antigen, c-Met(NP$_{13}$000236). In particular, the substitution of alanine (Ala) at the 94$^{th}$ position in CDR-L3 with arginine (Arg) (corresponding to clones L3D and L3E) and with histidine (His) (corresponding to clone L3A) leads to a more considerable increase in the binding ability to the antigen. In addition, in the case of the substitution at the 92$^{nd}$ position in CDR-L3 (Y92G; corresponding to L3F), the binding ability is also enhanced to some extent.

The above results indicate that the binding ability to the antigen, c-Met (NP_000236), can be increased by the substitution of only one amino acid residue at 94$^{th}$ position in CDR-L3 of the light chain variable region, and can be also enhanced a little by the substitution at 92$^{nd}$ position.

Example 5

Construction of a CDR Library for Affinity Maturation

Clone L3E, which shows the most excellent affinity in Example 4, is a completely humanized clone, wherein the framework of the light chain variable region is humanized using the gene of human germ line, IGKV2-28*01, and the framework of the heavy chain variable region is humanized using the gene of human germ line, IGHV3-72*01. The CDRs are derived from the mouse antibody AbF46, with the following modifications: a modification of 94$^{th}$ residue in CDR-L3 from Ala to Arg; and a modification of 34$^{th}$ residue in CDR-H1 from Met to Ile.

The clone L3E was used as a template on which CDR libraries were constructed. The amino acid sequences of CDRs used are summarized in Table 2:

TABLE 2

| CDRs of L3E | Amino acid sequence |
|---|---|
| CDR-H1 | DYY<u>I</u>S (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLAWGNQNNYLA (SEQ ID NO: 4) |
| CDR-L2 | WASTRVS (SEQ ID NO: 5) |
| CDR-L3 | QQSYS<u>R</u>PLT (SEQ ID NO: 6) |

CDR-L1 and CDR-H2 were too large to be made as a single library, so they were made in 2 separate libraries. Each library was designed so that all possible amino acids could be introduced into all possible positions of CDRs.

For use in the introduction of random sequences into the CDRs of the antibody, primers were designed as follows. In order to conduct completely random introduction into desired sites of mutation, the mixture where 4 bases are mixed at the same ratio (25% A, 25% G, 25% C, 25% T) was used for the random introduction of bases into CDRs of the antibody huAbF46.

The mutagenized DNAs were transformed into E. coli, and the resulting plaques were screened for binding to c-Met (NP_000236). The screening was accomplished by filter lifts in which filters coated with anti-human kappa light chain were placed onto agar plates with plaques obtained from the CDR libraries on the plate surface.

Fab produced from individual clones was captured by the anti-human kappa filter, and the filters were probed with biotinylated c-Met (NP_000236). Binding with the biotinylated c-Met (NP_000236) was visualized by the use of NeutrAvidin (Pierce, 31002) conjugated to alkaline phosphatase. Filters were probed with concentrations of biotinylated c-Met (NP_000236) that varied from 100 pM to 20 nM for 1 to 4 hours.

Figure 5:
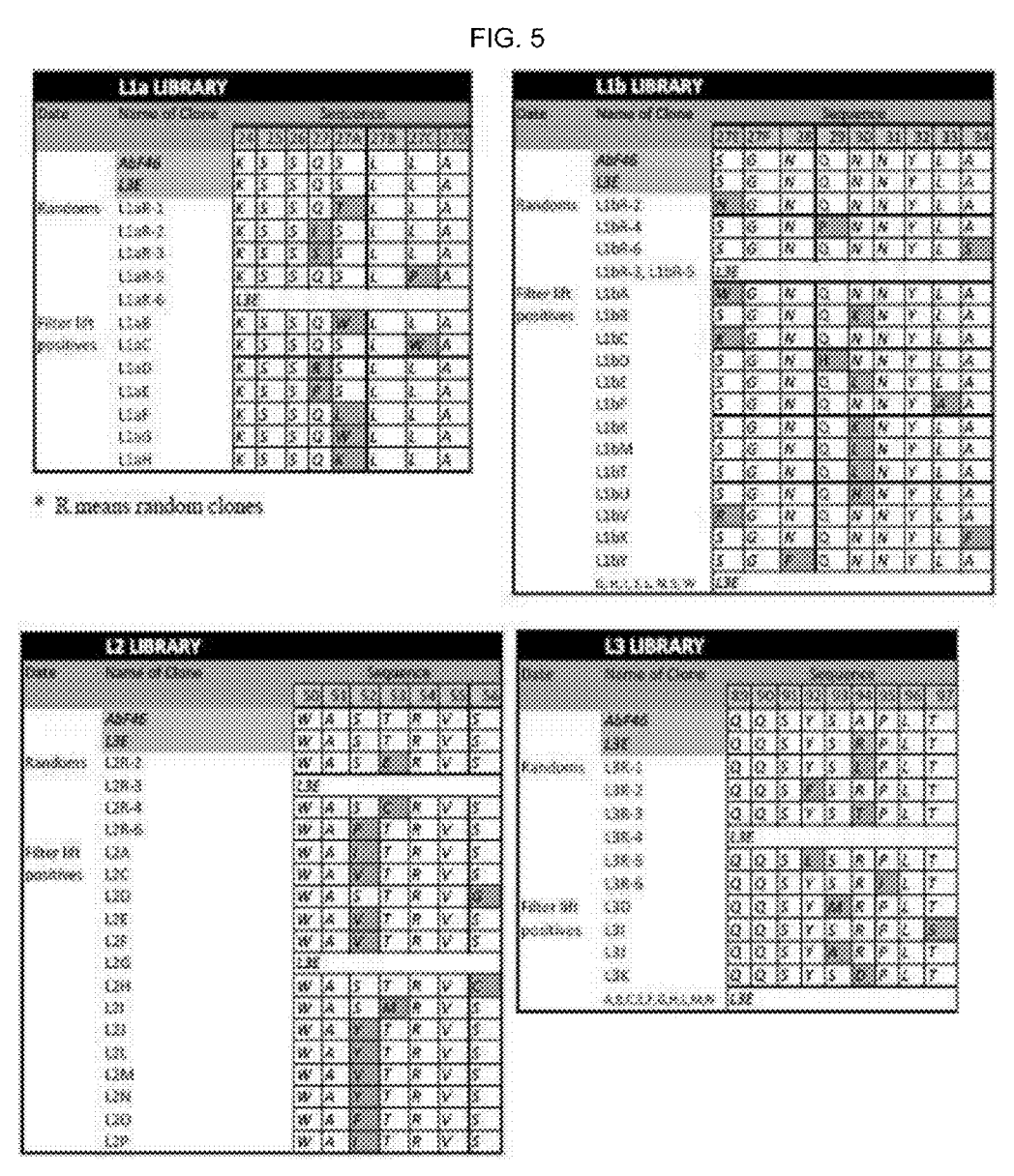
Figure 6:
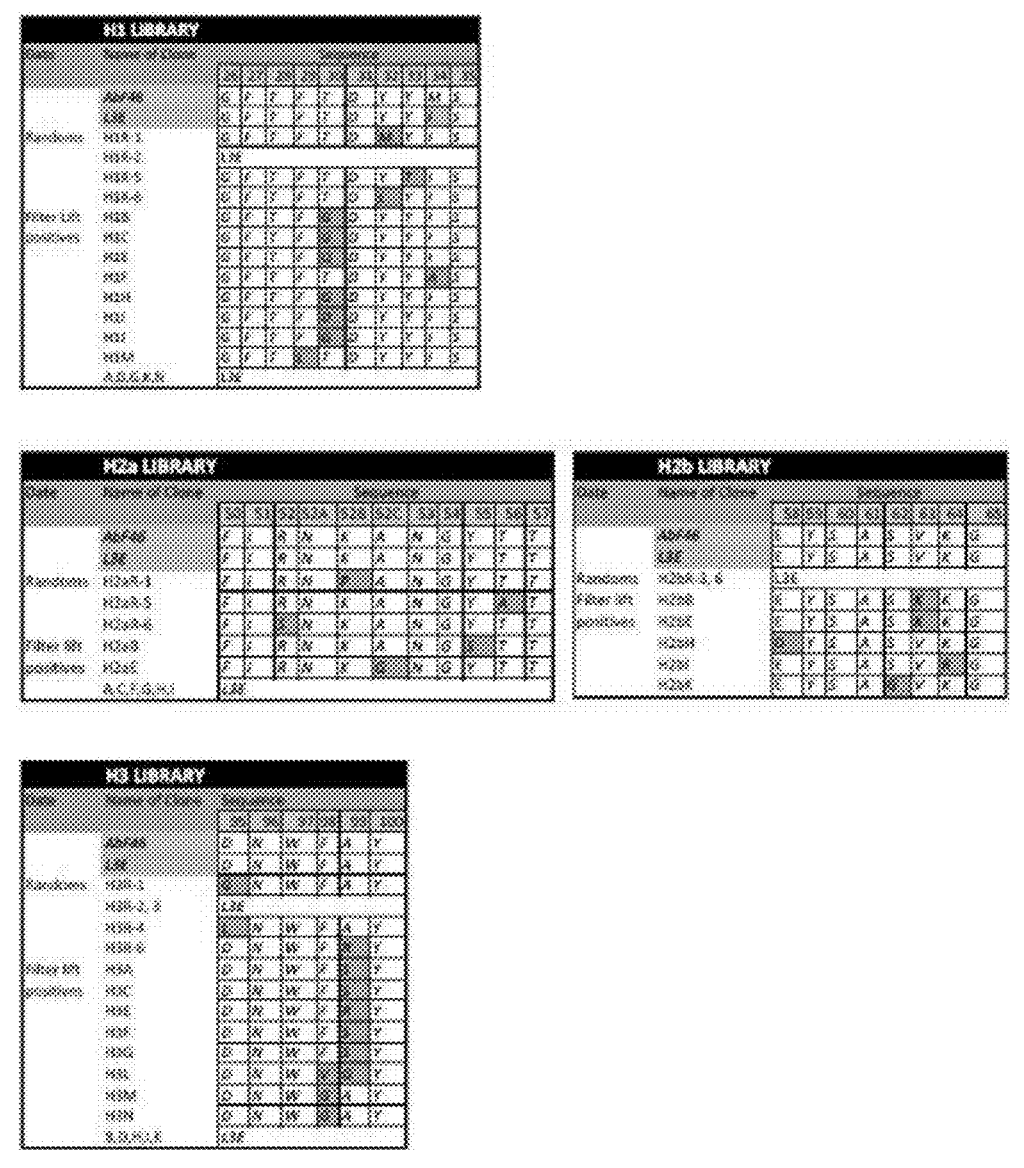

Referring to the method described in Example 4, a small amount of Fab was produced for each antibody. The produced Fab was quantified by ELISA, and the binding with c-Met (NP$_{13}$000236) was assayed by ELISA. The CDR sequences of clones sequenced at random and clones that were selected by filter lifts are shown in FIGS. 5 and 6.

The screening of the individual CDR libraries generated a wide diversity of sequences. The screening of some libraries, such as CDR-L2, chose mutations in a limited number of positions, while others, such as CDR-L3, selected mutations at many residues. All clones (humanized Fab) were tested for their ability to bind to c-Met (NP$_{13}$000236) in an ELISA format and examples of ELISA binding data are shown in FIGS. 7 and 8.

Figure 7:
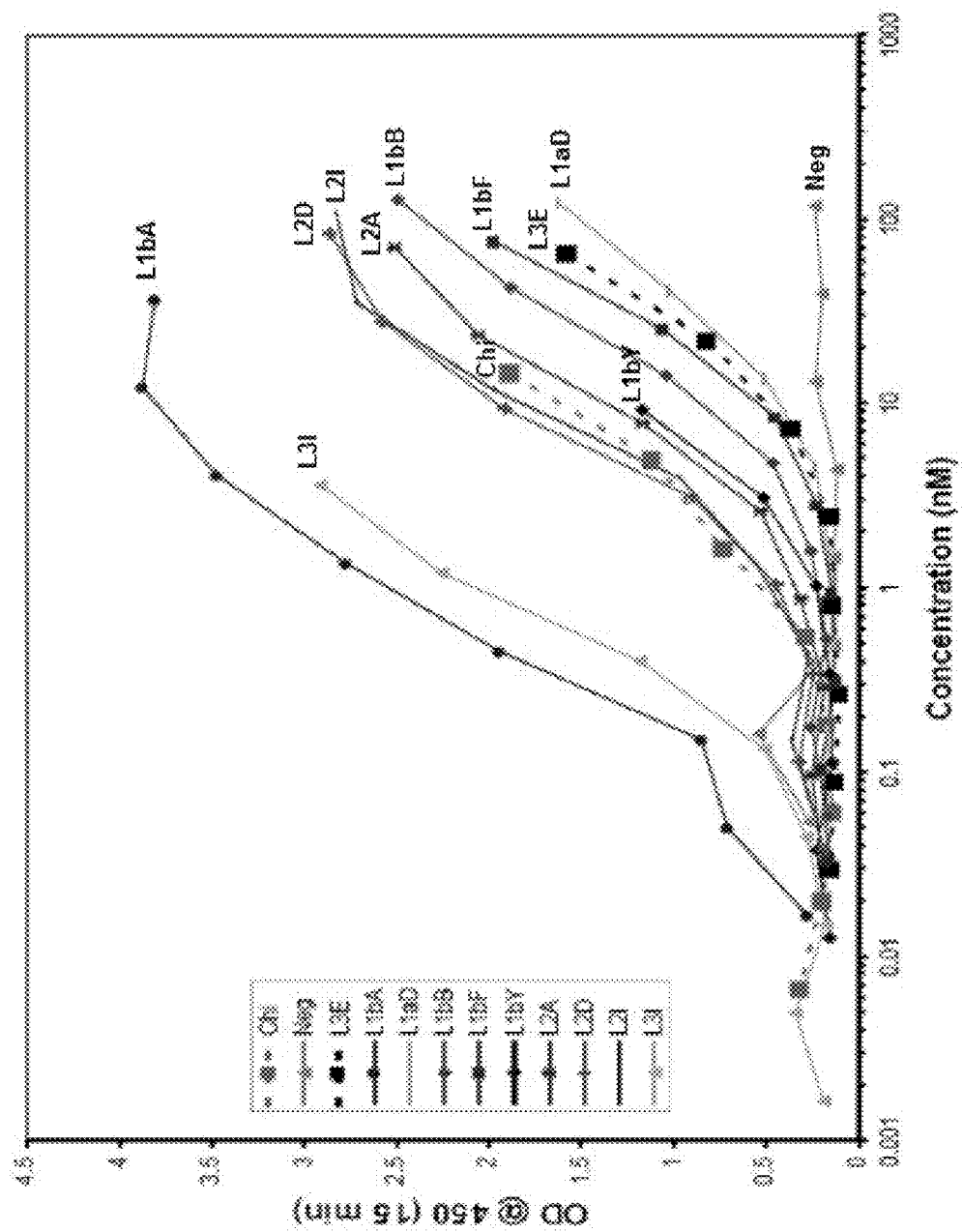
FIGS. 7 and 8 are graphs showing binding degrees of humanized Fabs derived from representative clones screened to the antigen, c-Met ($NP_{13}000236$). Absorbance at OD 450 nm (15 min) is indicated on the y-axis, and concentration (nM) is indicated on the x-axis.
Figure 8:
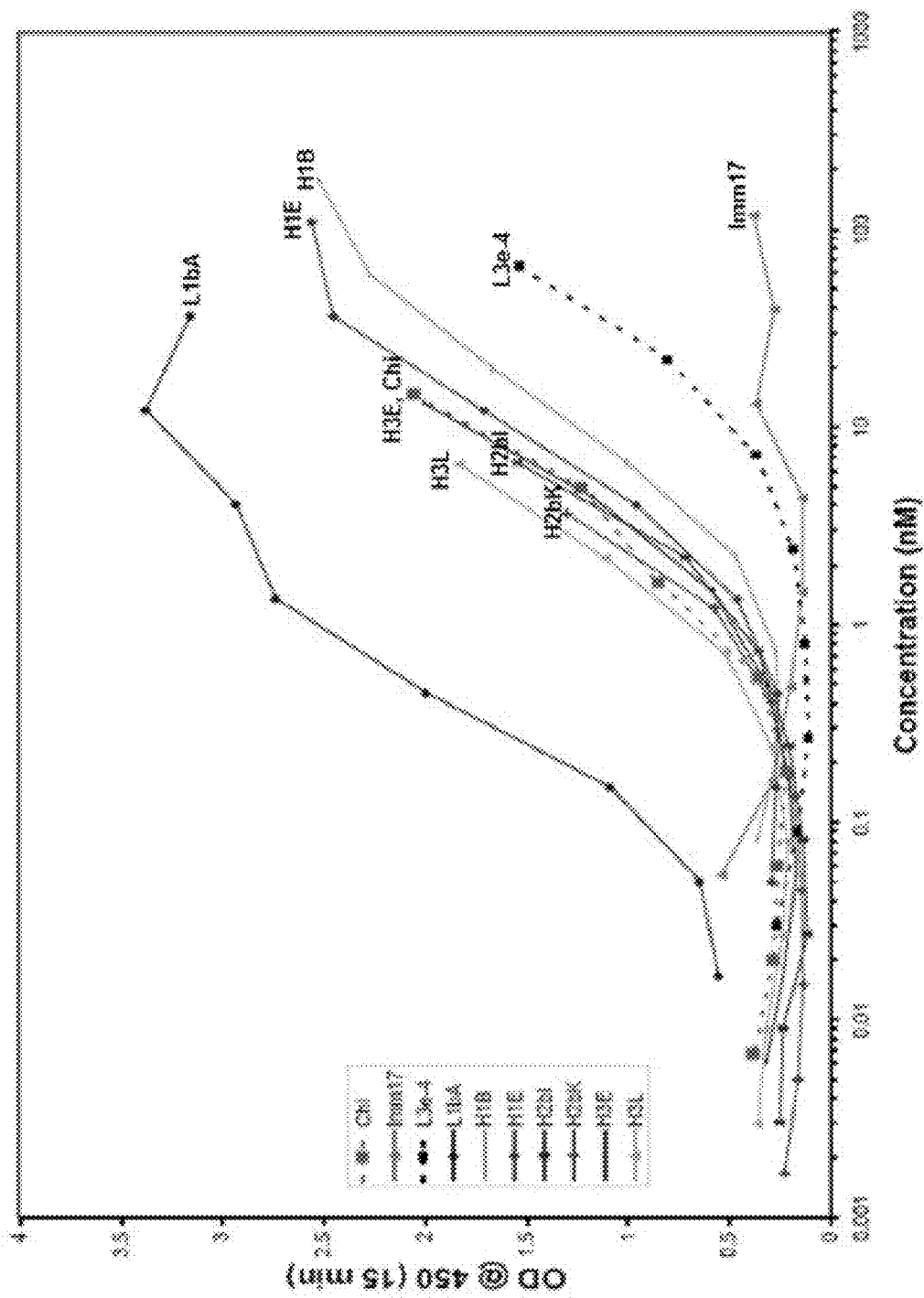

As shown in FIGS. 7 and 8, there were many CDR mutations that improved the binding of the template L3E. There were 2 mutations that had a profound impact on binding, and both of these were in the light chain. Clone L1bA (S27E→W) and clone L3I (T97→S) exhibited greatly improved binding abilities compared to the starting clone (template) L3E and far surpassed the binding ability of the chimeric clone. Based on several ELISAs, the Kd value of L3E was estimated to be about 30 nM, the Kd value of the chimeric clone was estimated to be about 4 nM, and the Kd value of the clone L1bA was estimated to be about 0.3 nM. The single mutation of clone L1bA (S27E→W) appears to have led to an improvement in binding of about 100-fold over the starting clone L3E.

Example 6

Construction of a Combinatorial Library

As the final step in the affinity maturation process, random combinations of the "best" mutations from the single CDR libraries were conducted to produce a combinatorial library. Clone L1bA that shows the most excellent affinity in Example 5 was chosen as the template for the combinatorial library. In addition, hot spots of the clones with improved affinity other than L1bA were analyzed, and additional affinity maturation was performed. Mutations (hot spots) randomly incorporated into the combinatorial library include the following:

| Clone | Mutation | Possible |
|---|---|---|
| L1bF | L33A | 2 |
| L1bY | N28F | 2 |
| L2A | S52I | 2 |
| L2D | S56G | 2 |
| L3I | T97S | 2 |
| H1E | T30Q | 2 |
| H2bI | K64R | 2 |
| H2bK | S62G | 2 |
| | | 256 |

Figure 9:
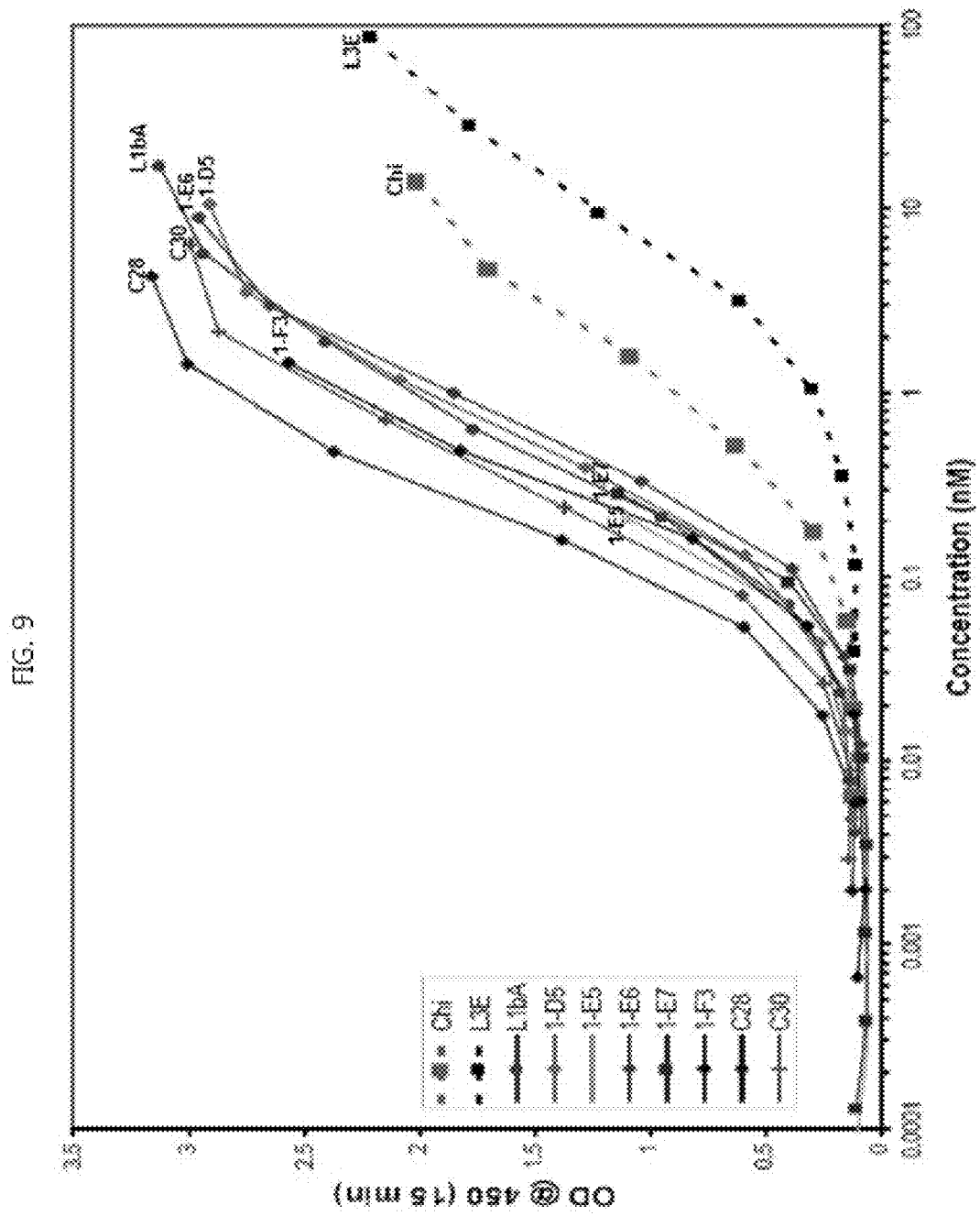
FIG. 9 is a graph showing binding degrees of humanized Fabs derived from clones screened from a combinatorial library to the antigen, c-Met ($NP_{13}000236$). Absorbance at OD 450 nm (15 min) is indicated on the y-axis, and concentration (nM) is indicated on the x-axis.

Two amino acids were introduced into each of the above hot spots (L33A (L1bF), N28F(L1bY), S52I(L2A), S56G (L2D), T97S(L3I), T30Q(H1E), K64R(H2bI), and S62G (H2bK)) before and after the mutation to construct 256 mutants in total. Binding abilities of the mutants to c-Met (NP$_{13}$000236) were assayed by ELISA (see FIG. 9).

Figure 10:
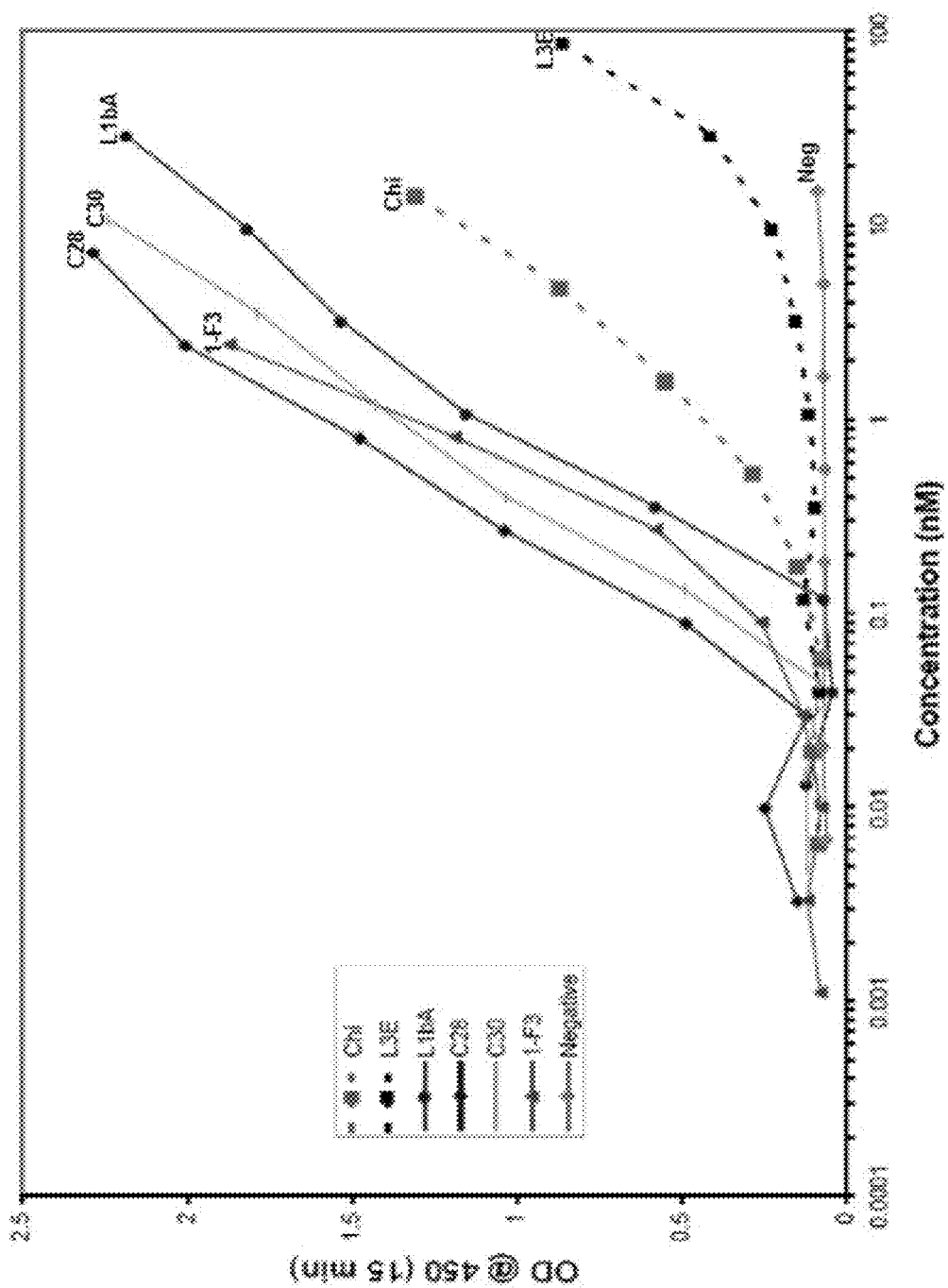
FIG. 10 is a graph showing binding degrees of humanized Fabs derived from clones selected from the result of FIG. 11 to the antigen, c-Met ($NP_{13}000236$). Absorbance at OD 450 nm (15 min) is indicated on the y-axis, and concentration (nM) is indicated on the x-axis.

Three clones with better binding than L1bA (starting clone for the combinatorial library) were identified, and named 1-F3, C28 and C30, respectively. Binding abilities of these clones to c-Met (NP$_{13}$000236) were re-assayed multiple times and representative results of those data are shown in FIG. 10. In FIG. 10, "negative" refers to the result from a phage in which no antibody fragment (scFv) is expressed.

An antibody fragment was designed based on C28 antibody, wherein L at the 46$^{th}$ position in VL was changed into M, Y at the 49$^{th}$ position in VL was changed into I, and L at the 96$^{th}$ position in VL was changed into Y. The gene encoding the antibody fragment was synthesized (Bioneer Inc.), and cloned into the same vector with that used for the wild-type to prepare a light chain of a mutated C28, namely antibody C28m.

Figure 11:
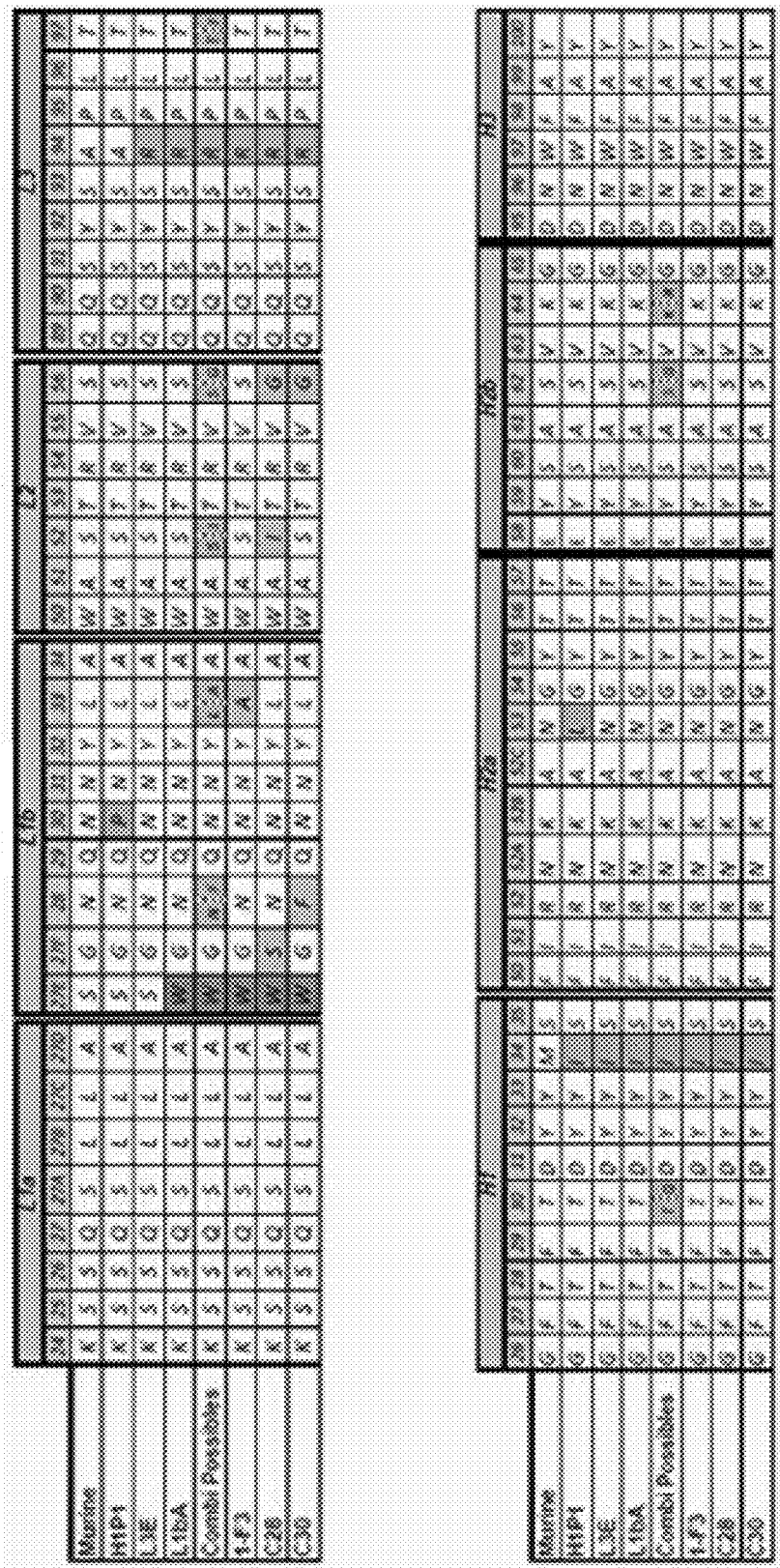
FIG. 11 illustrates a CDR sequence of an antibody finally prepared through humanization and affinity maturation.

The CDR sequences of the antibodies finally produced through the humanization, affinity maturation, and design of combinatorial library, as described above, are shown in FIG. 11, and sequences of heavy chain variable regions and light chain variable regions including the CDRs are shown in FIG. 12, as well as Tables 3 to 7.

TABLE 3

L1bA

| | Heavy chain | Light chain |
|---|---|---|
| variable region | EVQLVESGGG LVQPGGSLRL SCAASGFTFT DYYISWVRQA PGKGLEWVGF IRNKANGYTT EYSASVKGRF TISRDDSKNS LYLQMNSLKT EDTAVYYCAR DNWFAYWGQG TLVTVSS (SEQ ID NO: 13) | DILMTQSPSS LTVSAGEKVT MSCKSSQSLL ASGNQNNYLA HQQKPGRSP KMLIIWASTR VSGVPDRFIG SGSGTDFTLT INSVQAEDLA VYYCQQSYSA PLTFGAGTKL ELKRT (SEQ ID NO: 14) |
| CDR1 | DYYIS (SEQ ID NO: 1) | KSSQSLLAWGNQNNYLA (SEQ ID NO: 4) |
| CDR2 | FIRNKANGYTTEYSASVKG (SEQ ID NO: 2) | WASTRVS (SEQ ID NO: 5) |
| CDR3 | DNWFAY (SEQ ID NO: 3) | QQSYSRPLT (SEQ ID NO: 6) |

TABLE 4

C28

| | Heavy chain | Light chain |
|---|---|---|
| variable region | EVQLVESGGG LVQPGGSLRL SCAASGFTFT DYYISWVRQA PGKGLEWVGF IRNKANGYTT EYSASVKGRF TISRDDSKNS LYLQMNSLKT EDTAVYYCAR DNWFAYWGQG TLVTVSS (SEQ ID NO: 13) | DIVMTQSPLS LPVTPGEPAS ISCKSSQSLL AWSNQNNYLA WYLQKPGQSP QLLIYWAITR VGGVPDRFSG SGSGTDFTLK ISRVEAEDVG VYYCQQSYSR PLTFGQGTKL EIKRT (SEQ ID NO: 15) |
| CDR1 | DYYIS (SEQ ID NO: 1) | KSSQSLLAWSNQNNYLA (SEQ ID NO: 7) |
| CDR2 | FIRNKANGYTTEYSASVKG (SEQ ID NO: 2) | WAITRVG (SEQ ID NO: 11) |
| CDR3 | DNWFAY (SEQ ID NO: 3) | QQSYSRPLT (SEQ ID NO: 6) |

TABLE 5

C30

| | Heavy chain | Light chain |
|---|---|---|
| variable region | EVQLVESGGG LVQPGGSLRL SCAASGFTFT DYYISWVRQA PGKGLEWVGF IRNKANGYTT EYSASVKGRF TISRDDSKNS LYLQMNSLKT EDTAVYYCAR DNWFAYWGQG TLVTVSS (SEQ ID NO: 13) | DIVMTQSPLS LPVTPGEPAS ISCKSSQSLL AWGFQNNYLA WYLQKPGQSP QLLIYWASTR VGGVPDRFSG SGSGTDFTLK ISRVEAEDVG VYYCQQSYSR PLTFGQGTKL EIKRT (SEQ ID NO: 16) |
| CDR1 | DYYIS (SEQ ID NO: 1) | KSSQSLLAWGFQNNYLA (SEQ ID NO: 8) |
| CDR2 | FIRNKANGYTTEYSASVKG (SEQ ID NO: 2) | WASTRVG (SEQ ID NO: 10) |
| CDR3 | DNWFAY (SEQ ID NO: 3) | QQSYSRPLT (SEQ ID NO: 6) |

TABLE 6

1-F3

| | Heavy chain | Light chain |
|---|---|---|
| variable region | EVQLVESGGG LVQPGGSLRL SCAASGFTFT DYYISWVRQA PGKGLEWVGF IRNKANGYTT EYSASVKGRF TISRDDSKNS LYLQMNSLKT EDTAVYYCAR DNWFAYWGQG TLVTVSS (SEQ ID NO: 13) | DIVMTQSPLS LPVTPGEPAS ISCKSSQSLL AWGNQNNYAA WYLQKPGQSP QLLIYWASTR VSGVPDRFSG SGSGTDFTLK ISRVEAEDVG VYYCQQSYSR PLTFGQTKL EIKRT (SEQ ID NO: 17) |
| CDR1 | DYYIS (SEQ ID NO: 1) | KSSQSLLAWGNQNNYAA (SEQ ID NO: 9) |
| CDR2 | FIRNKANGYTTEYSASVKG (SEQ ID NO: 2) | WASTRVS (SEQ ID NO: 5) |
| CDR3 | DNWFAY (SEQ ID NO: 3) | QQSYSRPLT (SEQ ID NO: 6) |

TABLE 7

C28m

| | Heavy chain | Light chain |
|---|---|---|
| variable region | EVQLVESGGG LVQPGGSLRL SCAASGFTFT DYYISWVRQA PGKGLEWVGF IRNKANGYTT EYSASVKGRF TISRDDSKNS LYLQMNSLKT EDTAVYYCAR DNWFAYWGQG TLVTVSS (SEQ ID NO: 13) | DIVMTQSPLS LPVTPGEPAS ISCKSSQSLL AWSNQNNYLA WYLQKPGQSP QMLIIWAITR VGGVPDRFSG SGSGTDFTLK ISRVEAEDVG VYYCQQSYSR PYTFGQGTKL EIKRT (SEQ ID NO: 18) |
| CDR1 | DYYIS (SEQ ID NO: 1) | KSSQSLLAWSNQNNYLA (SEQ ID NO: 7) |
| CDR2 | FIRNKANGYTTEYSASVKG (SEQ ID NO: 2) | WAITRVG (SEQ ID NO: 11) |
| CDR3 | DNWFAY (SEQ ID NO: 3) | QQSYSRPYT (SEQ ID NO: 12) |

There were no specific patterns in the mutations of amino acid residues in light chains of combinatorial clones, and no mutation was observed in heavy chains. The binding abilities of the combinatorial clones were enhanced by about 3-fold. In addition, a considerable increase of binding ability was observed in clones L1bA (S27E->W) and L3E (A94->R). The Kd values of these clones were calculated and shown in Table 8:

TABLE 8

| Antibodies | $K_D$ (nM) | $k_s$ (1/Ms) | $k_d$ (1/s) | WT $K_D$/ Mutant $K_D$ |
|---|---|---|---|---|
| chAbF46 | 2.19 | $3.29 \times 10^5$ | $7.23 \times 10^{-4}$ | — |
| L1bA | 0.17 | $1.1 \times 10^5$ | $1.9 \times 10^{-4}$ | 12.8 |
| C28 | 0.11 | $1.0 \times 10^5$ | $1.0 \times 10^{-4}$ | 19.9 |
| C30 | 0.16 | $1.1 \times 10^5$ | $1.8 \times 10^{-4}$ | 13.7 |
| 1-F3 | 0.25 | $1.2 \times 10^5$ | $3.1 \times 10^{-4}$ | 8.8 |
| C28m | <0.01 | $9.4 \times 10^5$ | $<7.4 \times 10^{-5}$ | |

Example 7

Preparation of an Antibody

The polynucleotides encoding heavy chains and light chains of the screened antibodies were synthesized by Bioneer Inc., wherein the polynucleotides encoding heavy chains were designed so that each of them consists of a coding nucleotide sequence of 'EcoRI-signal sequence-VH-NheI-human IgG2 CH-XhoI' (wherein, VH refers to a heavy chain variable region of each antibody, and CH refers to a heavy chain constant region of each antibody); and the polynucleotides encoding light chains were designed so that each of them consists of a coding nucleotide sequence of 'EcoRI-signal sequence-VL-BsiWI-CL-XhoI' (wherein, VL refers to a light chain variable region of each antibody, and CL refers to a light chain constant region (kappa) of each antibody). Thereafter, the polynucleotide encoding the heavy chain and the polynucleotide encoding the light chain were digested with EcoRI (NEB, R0101S) and XhoI (NEB, R0146S) before cloning into a vector from the pOptiVEC™-TOPO TA Cloning Kit included in an OptiCHO™ Antibody Express Kit (Cat no. 12762-019, Invitrogen), and a vector from the pcDNA™3.3-TOPO TA Cloning Kit (Cat no. 8300-01), respectively, to construct vectors for expression of the antibodies.

Each of the vectors thus constructed was amplified with the aid of a Qiagen Maxiprep kit (Cat no. 12662). The vectors which respectively carried the heavy chain and the light chain were co-transfected at a ratio of 4:1 (80 μg:20 μg) into 293T cells (Invitrogen; $2.5 \times 10^7$ cells). The transfection into 293T cells ($2.5 \times 10^7$ cells) was performed in the presence of 360 μL of 2 M $CaCl_2$. Afterwards, the cells were incubated in DMEM supplemented with 10% (v/v) FBS for 5 hours at 37° C. under a 5% $CO_2$ conditions and then in FBS-free DMEM for 48 hours at 37° C. under 5% $CO_2$ conditions.

After centrifugation, the supernatant was applied to AKTA prime (GE Healthcare) to purify the antibodies. In this regard, 100 mL of the supernatant was loaded at a flow rate of 5 mL/min to AKTA Prime equipped with a Protein A column (GE Healthcare, Cat. no. 17-0405-03), followed by elution with an IgG elution buffer (Thermo Scientific, Cat. no. 21004). The buffer was exchanged with PBS buffer to purify the antibodies.

The sequences of the heavy chain variable regions, the light chain variable regions, and the CDRs are shown in Tables 3 to 7.

Example 8

Assay of the Bioactivities of the Screened Affinity Matured Antibodies (In vitro)

(1) BrdU Assay

In order to examine whether the affinity matured antibodies (L1bA, C28, C30, 1-F3, and C28m) prepared in Example 7 have any weakness in their stabilities, a BrdU assay was performed. A human lung cancer cell line, NCI-H441 (ATCC Cat. # HTB-174) was suspended in RPMI 1640 medium (Gibco) at the concentration of $2 \times 10^5$ cells/ml, and the obtained suspended solution was allotted to each 96-well tissue culture plate (Corning, Lowell, Mass.) at the amount of 100 μl per each plate. After culturing for 24 hours under the conditions of 37° C. and 5% $CO_2$, the medium was completely removed and substituted with a new RPMI 1640 medium in which each antibody was diluted. After culturing for 21 hours under the conditions of 37° C. and 5% $CO_2$, 5-bromo-2'-deoxyuridine (BrdU) was added thereto, further culturing continued for 3 hours, and then a BrdU assay (Roche, Indianapolis, Ind.) was performed.

After performing denaturation/fixation of the cultured cells on the plate, an anti-BrdU antibody (Roche) was added thereto. After 1 hour, a substrate was added, and then the color reaction was examined using ELISA spectraMax reader (Molecular Devices, Sunnyvale, Calif.) at 370 nm. The comparison was performed based on the agonism of the chimeric antibody AbF46. A well-known agonist, antibody 5D5 that was isolated and purified from ATCC Cat. # HB11895 hybridoma was used as a positive control.

Figure 13:
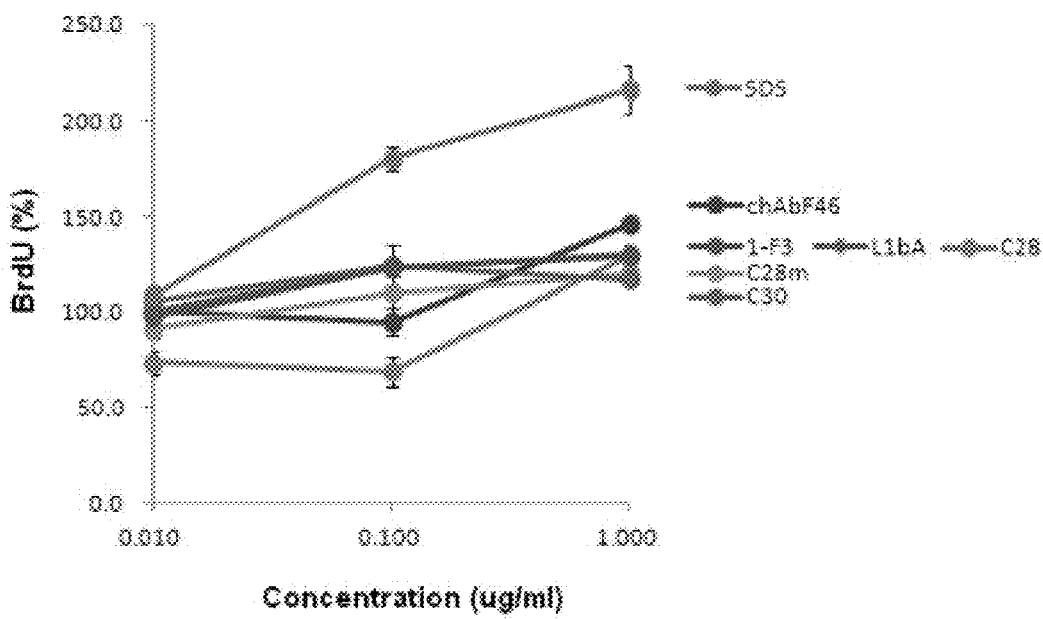
FIG. 13 is a graph showing results of BrdU assay for the antibody finally prepared through humanization and affinity maturation. BrdU (%) is indicated on the y-axis and concentration (μg/ml) is indicated on the x-axis.

The obtained results are shown in FIG. 13. As shown in FIG. 13, each of the 5 antibodies prepared as above exhibited decreased side effects of agonism, indicating that the stability is increased for all of the antibodies.

(2) Cell Proliferation Assay (In vitro)

In order to examine the anticancer effects of the 5 affinity matured antibodies prepared in Example 7 (by inhibiting the proliferation of cancer cells), an in vitro cell proliferation assay was conducted using a stomach cancer cell line MKN45 (Japanese Cancer Research Bank, JCRB, Tokyo, Japan) which expresses c-Met molecules on the cell surface.

MKN45 cells were seeded into 96-well plates at the amount of $1 \times 10^4$ cells per each well together with 50 μl of 5% FBS/DMEM media, and then, 50 μl of each of the 5 antibodies with various concentrations of 0.0016, 0.008, 0.04, 0.2, 1, and 5 μg/ml was added thereto. After culturing the obtained mixture for 72 hours under the conditions of 37° C. and 5% $CO_2$, the cell number was measured with a leuminometer (PerkinElmer, 2104 Multilabel reader) using CellTiter-Glo® Luminescent Cell Viability Assay Kit (Promega, G7570). The chimeric antibody AbF46 was used as a control group, and antibody 5D5 was used as a comparative group.

Figure 14:
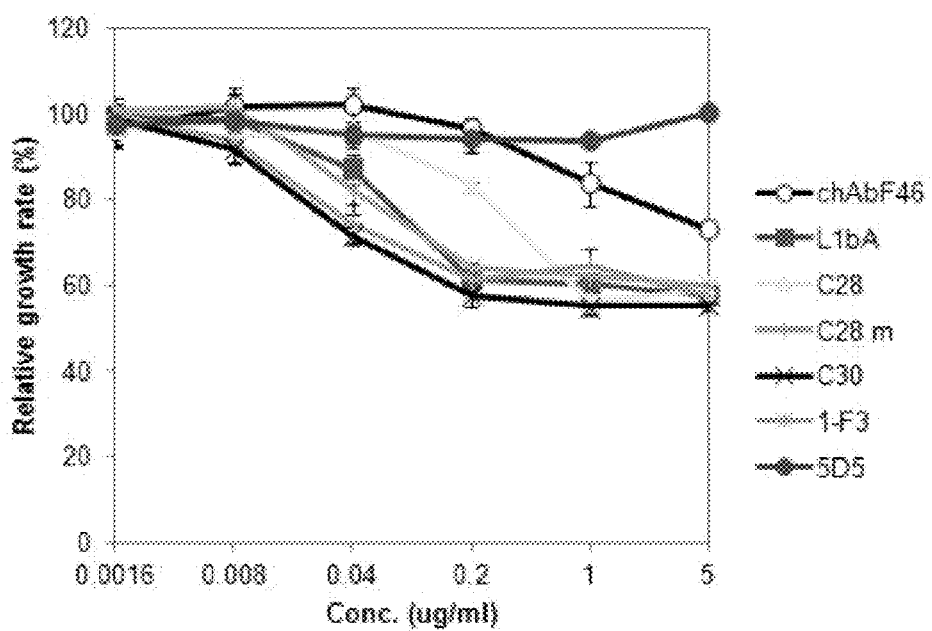
FIG. 14 is a graph showing the degree of inhibition against MKN45 cell proliferation by the antibody finally prepared through humanization and affinity maturation. Relative growth rate (%) is indicated on the y-axis and concentration (μg/ml) is indicated on the x-axis.

The obtained results are shown in FIG. 14. As shown in FIG. 14, each of the 5 antibodies exhibited considerably decreased cancer cell viability compared to antibody AbF46 and antibody 5D5, thereby exhibiting excellent anticancer effects.

(3) Akt Phosphorylation

The cellular activities controlled by Akt include cell proliferation, cell survival, control of cell size, reactivity to soluble nutrients, intermediate process of metabolism, angiogenesis, tissue invasion, and the like, all of which are representative characteristics of cancer, where lots of oncogenic proteins (oncoproteins) and lots of tumor suppressors affect each other in the manner of crossing over on the Akt pathway, and carry out a detailed regulation of cellular activities at the connecting point of signal transduction and classical metabolism control. Therefore, the increased level of phosphorylated Akt, which is an active form of Akt, indicates increased activity of cancer cells. The inhibition level against Akt phosphorylation by the 5 affinity matured antibodies was examined.

In order to compare the extent of agonism of the 5 affinity matured antibodies prepared in Example 7, the phosphorylation level of Akt protein was measured using Caki-1 cells (Korean Cell Line Bank). Medium was used as a negative control, and antibody 5D5 (known as an agonist) and antibody AbF46 were used as positive controls.

Caki-1 cells were seeded into 96-well plates in the amount of $2 \times 10^5$ cells/ml. After 24 hours, the cells were treated with 5 μg/ml of each antibody for 30 minutes under serum-free conditions. The antibody-treated cells were lysed, and then the Akt phosphorylation level was measured and analyzed using PathScan phospho-AKT1 (Ser473) chemiluminescent Sandwich ELISA kit (Cell Signaling, Cat. no. 7134S).

Figure 15:
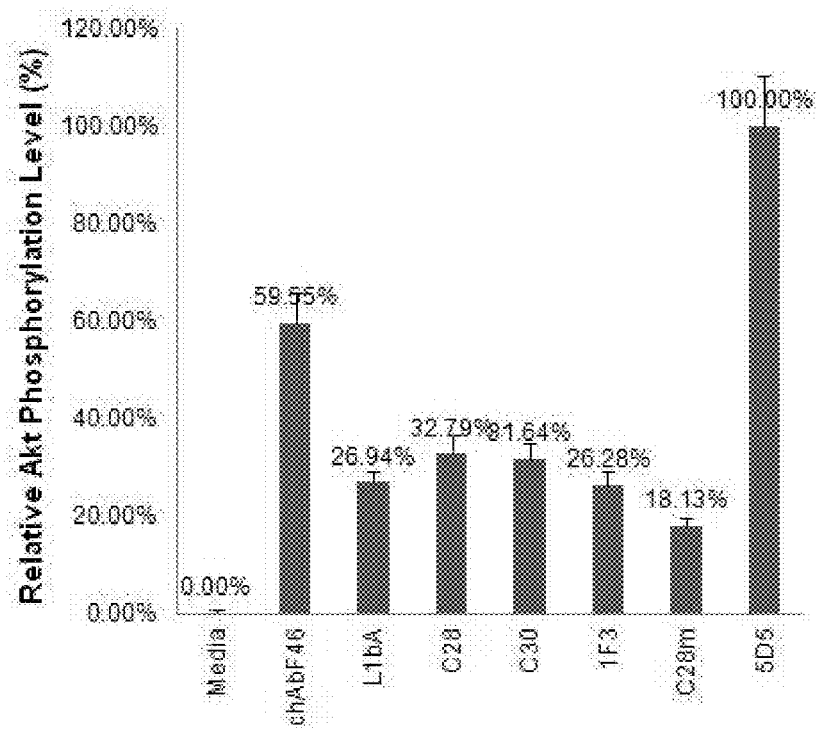
FIG. 15 is a graph showing the degree of phosphorylation by the antibody finally prepared through humanization and affinity maturation. Relative Akt phosphorylation level (%) is indicated on the y-axis and the particular antibody is indicated on the x-axis.

The obtained results are shown in FIG. 15. As shown in FIG. 15, each of the 5 antibodies exhibited an increased inhibition level against Akt phosphorylation compared to an antibody which is not subjected to affinity maturation.

(4) Examination of c-Met Degradation

In order to examine the anticancer effects of the 5 affinity matured antibodies prepared in Example 7, the level of degradation of c-Met protein by binding of each antibody was measured. This experiment is to examine the efficacy of the antibodies by measuring the total amount of c-Met protein on the basis that the binding of the antibody to c-Met leads to internalization and degradation of c-Met to decrease the total amount of c-Met.

$2 \times 10^5$ cells/ml of MKN45 cells were seeded into 96-well plates together with 5 μg/ml of each antibody and cultured for 24 hours. Thereafter, the antibody-treated cells were lysed and the change in the total amount of c-Met was measured and analyzed using Human total HGF R/c-MET ELISA KIT (R&D systems, DYC358).

Figure 16:
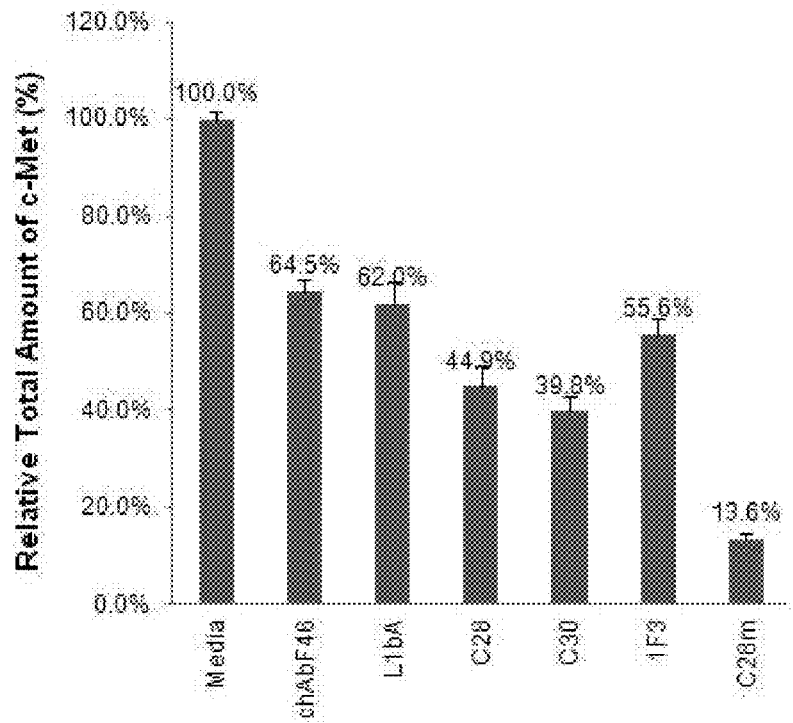
FIG. 16 is a graph showing the degree of c-Met degradation by the antibody finally prepared through humanization and affinity maturation. Relative total amount of c-Met (%) is indicated on the y-axis and the particular antibody is indicated on the x-axis.

The obtained results are shown in FIG. 16. As shown in FIG. 16, each of the 5 affinity matured antibodies exhibited an increased degradation level of c-Met compared to the chimeric antibody AbF46.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-c-Met antibody or an antigen-binding fragment thereof comprising:
    (a) a heavy chain variable region comprising (i) a CDR-H1 comprising the amino acid sequence of SEQ ID NO: 1, (ii) a CDR-H2 comprising the amino acid sequence of SEQ ID NO: 2, and (iii) a CDR-H3 comprising the amino acid sequence of SEQ ID NO: 3; and
    (b) a light chain variable region comprising (i) a CDR-L1 comprising the amino acid sequence of SEQ ID NO: 4, SEQ ID NO: 7, SEQ ID NO: 8, or SEQ ID NO: 9, (ii) a CDR-L2 comprising the amino acid sequence of SEQ ID NO: 5, SEQ ID NO: 10, or SEQ ID NO: 11, and (iii) a CDR-L3 comprising the amino acid sequence of SEQ ID NO: 6 or SEQ ID NO: 12.

2. The anti-c-Met antibody or an antigen-binding fragment thereof according to claim 1, comprising:
(a) a heavy chain variable region comprising the amino acid sequence of SEQ ID NO: 13, and
(b) a light chain variable region comprising the amino acid sequence of SEQ ID NO: 14, SEQ ID NO: 15, SEQ ID NO: 16, SEQ ID NO: 17, or SEQ ID NO: 18.

3. The anti-c-Met antibody or an antigen-binding fragment thereof according to claim 1, which has a c-Met binding affinity (Kd) of 1 nM or less.

4. The anti-c-Met antibody or an antigen-binding fragment thereof according to claim 1, wherein the antigen-binding fragment is selected from the group consisting of scFv, $(scFv)_2$, Fab, Fab', and $F(ab')_2$.

5. The anti-c-Met antibody or an antigen-binding fragment thereof according to claim 1, wherein the c-Met is human, monkey, mouse, or rat c-Met.

6. An anti-c-Met antibody or an antigen-binding fragment thereof that competes with the anti-c-Met antibody or an antigen-binding fragment thereof according to claim 1 for binding to c-Met.

7. The anti-c-Met antibody or an antigen-binding fragment thereof according to claim 6, which has a c-Met binding affinity (Kd) of 1 nM or less.

8. The anti-c-Met antibody or an antigen-binding fragment thereof according to claim 6, wherein the antigen-binding fragment is selected from the group consisting of scFv, $(scFv)_2$, Fab, Fab', and $F(ab')_2$.

9. The anti-c-Met antibody or an antigen-binding fragment thereof according to claim 6, wherein the c-Met is human, monkey, mouse, or rat c-Met.

10. A nucleic acid encoding the anti-c-Met antibody or antibody fragment of claim 1, or fragment thereof comprising the heavy chain variable region or light chain variable region.

11. A vector comprising the nucleic acid of claim 10.

* * * * *

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: CDR-H1

<400> SEQUENCE: 1

Asp Tyr Tyr Ile Ser
  1               5

<210> SEQ ID NO 2
<211> LENGTH: 19
<212> TYPE: PRT
<213> ORGANISM: Artificial Sequence
```

```
<220> FEATURE:
<223> OTHER INFORMATION: CDR-H2

<400> SEQUENCE: 2

Phe Ile Arg Asn Lys Ala Asn Gly Tyr Thr Thr Glu Tyr Ser Ala Ser
  1               5                  10                  15
Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: CDR-H3

<400> SEQUENCE: 3

Asp Asn Trp Phe Ala Tyr
  1               5

<210> SEQ ID NO 4
<211> LENGTH: 17
<212> TYPE: PRT
<213> ORGANISM: Artificial Sequence
<220> FEATURE:
<223> OTHER INFORMATION: CDR-L1 of L1bA

<400> SEQUENCE: 4

Lys Ser Ser Gln Ser Leu Leu Ala Trp Gly Asn Gln Asn Asn Tyr Leu
  1               5                  10                  15
Ala

<210> SEQ ID NO 5
<211> LENGTH: 7
<212> TYPE: PRT
<213> ORGANISM: Artificial Sequence
<220> FEATURE:
<223> OTHER INFORMATION: CDR-L2 of L1bA and 1-F3

<400> SEQUENCE: 5

Trp Ala Ser Thr Arg Val Ser
  1               5

<210> SEQ ID NO 6
<211> LENGTH: 9
<212> TYPE: PRT
<213> ORGANISM: Artificial Sequence
<220> FEATURE:
<223> OTHER INFORMATION: CDR-L3 of L1bA, 1-F3, C28, and C30

<400> SEQUENCE: 6

Gln Gln Ser Tyr Ser Arg Pro Leu Thr
  1               5

<210> SEQ ID NO 7
<211> LENGTH: 17
<212> TYPE: PRT
<213> ORGANISM: Artificial Sequence
<220> FEATURE:
<223> OTHER INFORMATION: CDR-L1 of C28 and C28m

<400> SEQUENCE: 7

Lys Ser Ser Gln Ser Leu Leu Ala Trp Ser Asn Gln Asn Asn Tyr Leu
  1               5                  10                  15
Ala
```

```
<210> SEQ ID NO 8
<211> LENGTH: 17
<212> TYPE: PRT
<213> ORGANISM: Artificial Sequence
<220> FEATURE:
<223> OTHER INFORMATION: CDR-L1 of C30

<400> SEQUENCE: 8

Lys Ser Ser Gln Ser Leu Leu Ala Trp Gly Phe Gln Asn Asn Tyr Leu
 1               5                  10                  15

Ala

<210> SEQ ID NO 9
<211> LENGTH: 17
<212> TYPE: PRT
<213> ORGANISM: Artificial Sequence
<220> FEATURE:
<223> OTHER INFORMATION: CDR-L1 of 1-F3

<400> SEQUENCE: 9

Lys Ser Ser Gln Ser Leu Leu Ala Trp Gly Asn Gln Asn Asn Tyr Ala
 1               5                  10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: CDR-L2 of C30

<400> SEQUENCE: 10

Trp Ala Ser Thr Arg Val Gly
 1               5

<210> SEQ ID NO 11
<211> LENGTH: 7
<212> TYPE: PRT
<213> ORGANISM: Artificial Sequence
<220> FEATURE:
<223> OTHER INFORMATION: CDR-L2 of C28 and C28m

<400> SEQUENCE: 11

Trp Ala Ile Thr Arg Val Gly
 1               5

<210> SEQ ID NO 12
<211> LENGTH: 9
<212> TYPE: PRT
<213> ORGANISM: Artificial Sequence
<220> FEATURE:
<223> OTHER INFORMATION: CDR-L3 of C28m

<400> SEQUENCE: 12

Gln Gln Ser Tyr Ser Arg Pro Tyr Thr
 1               5

<210> SEQ ID NO 13
<211> LENGTH: 117
<212> TYPE: PRT
<213> ORGANISM: Artificial Sequence
<220> FEATURE:
<223> OTHER INFORMATION: heavy chain variable region of L1bA, 1-F3, C28,
      C28m, and C30

<400> SEQUENCE: 13
```

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Ile Ser Trp Val Arg Gln Ala Pro Gly Lys Gly Leu Glu Trp Val
         35                  40                  45

Gly Phe Ile Arg Asn Lys Ala Asn Gly Tyr Thr Thr Glu Tyr Ser Ala
         50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: light chain variable region of L1bA

<400> SEQUENCE: 14

Asp Ile Val Met Thr Gln Ser Pro Leu Ser Leu Pro Val Thr Pro Gly
  1               5                  10                  15

Glu Pro Ala Ser Ile Ser Cys Lys Ser Ser Gln Ser Leu Leu Ala Trp
             20                  25                  30

Gly Asn Gln Asn Asn Tyr Leu Ala Trp Tyr Leu Gln Lys Pro Gly Gln
         35                  40                  45

Ser Pro Gln Leu Leu Ile Tyr Trp Ala Ser Thr Arg Val Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Arg Pro Leu Thr Phe Gly Gln Gly Thr Lys Leu Glu Ile
            100                 105                 110

Lys Arg Thr
        115

<210> SEQ ID NO 15
<211> LENGTH: 115
<212> TYPE: PRT
<213> ORGANISM: Artificial Sequence
<220> FEATURE:
<223> OTHER INFORMATION: light chain variable region of C28

<400> SEQUENCE: 15

Asp Ile Val Met Thr Gln Ser Pro Leu Ser Leu Pro Val Thr Pro Gly
  1               5                  10                  15

Glu Pro Ala Ser Ile Ser Cys Lys Ser Ser Gln Ser Leu Leu Ala Trp
             20                  25                  30

Ser Asn Gln Asn Asn Tyr Leu Ala Trp Tyr Leu Gln Lys Pro Gly Gln
         35                  40                  45

Ser Pro Gln Leu Leu Ile Tyr Trp Ala Ile Thr Arg Val Gly Gly Val
```

```
            50                  55                  60
Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Arg Pro Leu Thr Phe Gly Gln Gly Thr Lys Leu Glu Ile
                100                 105                 110

Lys Arg Thr
        115
```

<210> SEQ ID NO 16
<211> LENGTH: 115
<212> TYPE: PRT
<213> ORGANISM: Artificial Sequence
<220> FEATURE:
<223> OTHER INFORMATION: light chain variable region of C30

<400> SEQUENCE: 16

```
Asp Ile Val Met Thr Gln Ser Pro Leu Ser Leu Pro Val Thr Pro Gly
 1               5                  10                  15

Glu Pro Ala Ser Ile Ser Cys Lys Ser Ser Gln Ser Leu Leu Ala Trp
                 20                  25                  30

Gly Phe Gln Asn Asn Tyr Leu Ala Trp Tyr Leu Gln Lys Pro Gly Gln
             35                  40                  45

Ser Pro Gln Leu Leu Ile Tyr Trp Ala Ser Thr Arg Val Gly Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Arg Pro Leu Thr Phe Gly Gln Gly Thr Lys Leu Glu Ile
                100                 105                 110

Lys Arg Thr
        115
```

<210> SEQ ID NO 17
<211> LENGTH: 115
<212> TYPE: PRT
<213> ORGANISM: Artificial Sequence
<220> FEATURE:
<223> OTHER INFORMATION: light chain variable region of 1-F3

<400> SEQUENCE: 17

```
Asp Ile Val Met Thr Gln Ser Pro Leu Ser Leu Pro Val Thr Pro Gly
 1               5                  10                  15

Glu Pro Ala Ser Ile Ser Cys Lys Ser Ser Gln Ser Leu Leu Ala Trp
                 20                  25                  30

Gly Asn Gln Asn Asn Tyr Ala Ala Trp Tyr Leu Gln Lys Pro Gly Gln
             35                  40                  45

Ser Pro Gln Leu Leu Ile Tyr Trp Ala Ser Thr Arg Val Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Arg Pro Leu Thr Phe Gly Gln Gly Thr Lys Leu Glu Ile
                100                 105                 110
```

```
Lys Arg Thr
        115

<210> SEQ ID NO 18
<211> LENGTH: 115
<212> TYPE: PRT
<213> ORGANISM: Artificial Sequence
<220> FEATURE:
<223> OTHER INFORMATION: light chain variable region of C28m

<400> SEQUENCE: 18

Asp Ile Val Met Thr Gln Ser Pro Leu Ser Leu Pro Val Thr Pro Gly
  1               5                  10                  15

Glu Pro Ala Ser Ile Ser Cys Lys Ser Ser Gln Ser Leu Leu Ala Trp
             20                  25                  30

Ser Asn Gln Asn Asn Tyr Leu Ala Trp Tyr Leu Gln Lys Pro Gly Gln
         35                  40                  45

Ser Pro Gln Met Leu Ile Ile Trp Ala Ile Thr Arg Val Gly Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Arg Pro Tyr Thr Phe Gly Gln Gly Thr Lys Leu Glu Ile
            100                 105                 110

Lys Arg Thr
        115

<210> SEQ ID NO 19
<211> LENGTH: 117
<212> TYPE: PRT
<213> ORGANISM: Artificial Sequence
<220> FEATURE:
<223> OTHER INFORMATION: heavy chain variable region of chAbF46

<400> SEQUENCE: 19

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Ala Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Gln Ser Ile
 65                  70                  75                  80

Leu Tyr Leu Gln Met Asp Thr Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 20
<211> LENGTH: 115
<212> TYPE: PRT
<213> ORGANISM: Artificial Sequence
<220> FEATURE:
<223> OTHER INFORMATION: light chain variable region of chAbF46
```

```
<400> SEQUENCE: 20

Asp Ile Leu Met Thr Gln Ser Pro Ser Ser Leu Thr Val Ser Ala Gly
 1               5                  10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg Thr
        115

<210> SEQ ID NO 21
<211> LENGTH: 444
<212> TYPE: PRT
<213> ORGANISM: Artificial Sequence
<220> FEATURE:
<223> OTHER INFORMATION: SEMA domain of c-Met

<400> SEQUENCE: 21

Leu His Glu His His Ile Phe Leu Gly Ala Thr Asn Tyr Ile Tyr Val
 1               5                  10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
```

```
                225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
                260                 265                 270

Leu Ala Arg Gln Ile Gly Ala Ser Leu Asn Asp Asp Ile Leu Phe Gly
                275                 280                 285

Val Phe Ala Gln Ser Lys Pro Asp Ser Ala Glu Pro Met Asp Arg Ser
            290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
        370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
                420                 425                 430

Glu Val Ile Val Glu His Thr Leu Asn Gln Asn Gly
            435                 440

<210> SEQ ID NO 22
<211> LENGTH: 19
<212> TYPE: PRT
<213> ORGANISM: Artificial Sequence
<220> FEATURE:
<223> OTHER INFORMATION: epitope in SEMA domain of c-Met

<400> SEQUENCE: 22

Phe Ser Pro Gln Ile Glu Glu Pro Ser Gln Cys Pro Asp Cys Val Val
1               5                   10                  15

Ser Ala Leu

<210> SEQ ID NO 23
<211> LENGTH: 10
<212> TYPE: PRT
<213> ORGANISM: Artificial Sequence
<220> FEATURE:
<223> OTHER INFORMATION: epitope in SEMA domain of c-Met

<400> SEQUENCE: 23

Pro Gln Ile Glu Glu Pro Ser Gln Cys Pro
1               5                   10

<210> SEQ ID NO 24
<211> LENGTH: 5
<212> TYPE: PRT
<213> ORGANISM: Artificial Sequence
<220> FEATURE:
<223> OTHER INFORMATION: epitope in SEMA domain of c-Met

<400> SEQUENCE: 24
```

Glu Glu Pro Ser Gln
1               5

<210> SEQ ID NO 25
<211> LENGTH: 13
<212> TYPE: PRT
<213> ORGANISM: Artificial Sequence
<220> FEATURE:
<223> OTHER INFORMATION: modified hinge region(U7-HC6)

<400> SEQUENCE: 25

Glu Pro Ser Cys Asp Lys His Cys Cys Pro Pro Cys Pro
1               5                   10

<210> SEQ ID NO 26
<211> LENGTH: 13
<212> TYPE: PRT
<213> ORGANISM: Artificial Sequence
<220> FEATURE:
<223> OTHER INFORMATION: modified hinge region(U6-HC7)

<400> SEQUENCE: 26

Glu Pro Lys Ser Cys Asp Cys His Cys Pro Pro Cys Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: modified hinge region(U3-HC9)

<400> SEQUENCE: 27

Glu Arg Lys Cys Cys Val Glu Cys Pro Pro Cys Pro
1               5                   10

<210> SEQ ID NO 28
<211> LENGTH: 14
<212> TYPE: PRT
<213> ORGANISM: Artificial Sequence
<220> FEATURE:
<223> OTHER INFORMATION: modified hinge region(U6-HC8)

<400> SEQUENCE: 28

Glu Pro Arg Asp Cys Gly Cys Lys Pro Cys Pro Pro Cys Pro
1               5                   10

<210> SEQ ID NO 29
<211> LENGTH: 13
<212> TYPE: PRT
<213> ORGANISM: Artificial Sequence
<220> FEATURE:
<223> OTHER INFORMATION: modified hinge region(U8-HC5)

<400> SEQUENCE: 29

Glu Lys Cys Asp Lys Thr His Thr Cys Pro Pro Cys Pro
1               5                   10

<210> SEQ ID NO 30
<211> LENGTH: 15
<212> TYPE: PRT
<213> ORGANISM: Artificial Sequence
<220> FEATURE:
<223> OTHER INFORMATION: human hinge region

<400> SEQUENCE: 30

Glu Pro Lys Ser Cys Asp Lys Thr His Thr Cys Pro Pro Cys Pro

<210> SEQ ID NO 31
<211> LENGTH: 5
<212> TYPE: PRT
<213> ORGANISM: Artificial Sequence
<220> FEATURE:
<223> OTHER INFORMATION: CDR-H1 of chAbF46

<400> SEQUENCE: 31

Asp Tyr Tyr Met Ser
1               5

<210> SEQ ID NO 32
<211> LENGTH: 17
<212> TYPE: PRT
<213> ORGANISM: Artificial Sequence
<220> FEATURE:
<223> OTHER INFORMATION: CDR-L1 of chAbF46

<400> SEQUENCE: 32

Lys Ser Ser Gln Ser Leu Leu Ala Ser Gly Asn Gln Asn Asn Tyr Leu
1               5                   10                  15

Ala

<210> SEQ ID NO 33
<211> LENGTH: 9
<212> TYPE: PRT
<213> ORGANISM: Artificial Sequence
<220> FEATURE:
<223> OTHER INFORMATION: CDR-L3 of chAbF46

<400> SEQUENCE: 33

Gln Gln Ser Tyr Ser Ala Pro Leu Thr
1               5

<210> SEQ ID NO 34
<211> LENGTH: 5
<212> TYPE: PRT
<213> ORGANISM: Artificial Sequence
<220> FEATURE:
<223> OTHER INFORMATION: N-terminal amino acide sequence of CDR-H1 in
      other numbering scheme than kabat numbering scheme

<400> SEQUENCE: 34

Gly Phe Thr Phe Thr
1               5

<210> SEQ ID NO 35
<211> LENGTH: 100
<212> TYPE: PRT
<213> ORGANISM: Artificial Sequence
<220> FEATURE:
<223> OTHER INFORMATION: IGKV2-28*01

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro
        100

<210> SEQ ID NO 36
<211> LENGTH: 342
<212> TYPE: DNA
<213> ORGANISM: Artificial Sequence
<220> FEATURE:
<223> OTHER INFORMATION: DNA sequence coding VL of AbF46

<400> SEQUENCE: 36
gatattgtga tgactcagtc tccactctcc ctgcccgtca cccctggaga gccggcctcc      60
atctcctgca gtccagtca gagtctttta gctagtggca accaaccaaa ctacttggcc      120
tggtacctgc agaagccagg gcagtctcca cagctcctga tctattgggc atccrctagg    180
gtatctgggg tccctgacag gttcagtggc agtggatcag gcacagattt tacactgaaa    240
atcagcagag tggaggctga ggatgttggg gtttattact gccagcagtc ctacagcgct    300
ccgctcacgt ttggccaggg gaccaagctg gagatcaaac ga                        342

<210> SEQ ID NO 37
<211> LENGTH: 100
<212> TYPE: PRT
<213> ORGANISM: Artificial Sequence
<220> FEATURE:
<223> OTHER INFORMATION: IGHV3-72*01

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg
        100

<210> SEQ ID NO 38
<211> LENGTH: 351
<212> TYPE: DNA
<213> ORGANISM: Artificial Sequence
<220> FEATURE:
<223> OTHER INFORMATION: DNA sequence coding VH of AbF46

<400> SEQUENCE: 38
gaggtgcagc tggtggagtc tgggggaggc ttggtccagc ctggagggtc cctgagactc      60
tcctgtgcag cctctgggtt caccttcact gattactaca taagctgggt ccgccaggct    120
ccagggaagg ggctggagtg ggttggcttt attagaaaca aagccctagg ttacacaaca    180
gagtacagtg catctgtgab gggtagattc accatctcaa gagatgattc aaagaactca    240

```
ctgtatctgc aaatgaacag cctgaaaacc gaggacacgg ccgtgtatta ctgtgctaga    300
gataactggt ttgcttbctg gggccagggc accctggtca ccgtctcctc a            351
```

<210> SEQ ID NO 39
<211> LENGTH: 114
<212> TYPE: PRT
<213> ORGANISM: Artificial Sequence
<220> FEATURE:
<223> OTHER INFORMATION: VL of humanized AbF46

<400> SEQUENCE: 39

```
Asp Ile Val Met Thr Gln Ser Pro Leu Ser Leu Pro Val Thr Pro Gly
 1               5                  10                  15

Glu Pro Ala Ser Ile Ser Cys Lys Ser Ser Gln Ser Leu Leu Ala Ser
            20                  25                  30

Gly Asn Gln Pro Asn Tyr Leu Ala Trp Tyr Leu Gln Lys Pro Gly Gln
        35                  40                  45

Ser Pro Gln Leu Leu Ile Tyr Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Asx Asp Val Gly Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys Arg
```

<210> SEQ ID NO 40
<211> LENGTH: 117
<212> TYPE: PRT
<213> ORGANISM: Artificial Sequence
<220> FEATURE:
<223> OTHER INFORMATION: VH of humanized AbF46

<400> SEQUENCE: 40

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Ile Ser Trp Val Arg Gln Ala Pro Gly Lys Gly Leu Glu Trp Val
        35                  40                  45

Gly Phe Ile Arg Asn Lys Ala Leu Gly Tyr Thr Thr Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115
```